United States Patent
Shue et al.

[11] Patent Number: 5,892,039
[45] Date of Patent: Apr. 6, 1999

[54] PIPERAZINO DERIVATIVES AS NEUROKININ ANTAGONISTS

[75] Inventors: Ho-Jane Shue, Pine Brook; Neng-Yang Shih; David J. Blythin, both of North Caldwell; Xiao Chen, Edison; John J. Piwinski, Clinton Township; Kevin D. McCormick, Edison, all of N.J.

[73] Assignee: Schering Corporation, Kenilworth, N.J.

[21] Appl. No.: 706,016

[22] Filed: Aug. 30, 1996

Related U.S. Application Data

[63] Continuation-in-part of Ser. No. 663,880, Jun. 14, 1996, Pat. No. 5,795,894, which is a continuation-in-part of PCT/US96/05660, May 1, 1996.

[60] Provisional application No. 60/003,048 Aug. 31, 1995.

[30] Foreign Application Priority Data

May 1, 1996 [WO] WIPO ............................. US 96/05660

[51] Int. Cl.⁶ ...................... A61K 31/495; C07D 401/02; C07D 401/14
[52] U.S. Cl. .......................... 544/360; 544/364; 544/357; 544/387; 514/252; 514/253; 514/255
[58] Field of Search ................................... 544/360, 364; 514/252, 253

[56] References Cited

U.S. PATENT DOCUMENTS

| | | | |
|---|---|---|---|
| 3,935,214 | 1/1976 | Zellner | 544/360 |
| 4,935,419 | 6/1990 | Bjork et al. | 514/231.5 |
| 5,350,852 | 9/1994 | Emonds-Alt et al. | 544/336 |
| 5,464,788 | 11/1995 | Bock et al. | 514/252 |
| 5,654,316 | 8/1997 | Carruthers et al. | 514/307 |
| 5,688,960 | 11/1997 | Shankar | 546/202 |
| 5,691,362 | 11/1997 | McCormick et al. | 546/277.4 |
| 5,719,156 | 2/1998 | Shue et al. | 514/255 |
| 5,795,894 | 8/1998 | Shue et al. | 514/253 |

FOREIGN PATENT DOCUMENTS

| | | |
|---|---|---|
| 0 655 442 | 5/1995 | European Pat. Off. |
| 655442 | 5/1995 | European Pat. Off. |
| 2230262 | 10/1990 | United Kingdom |
| WO 92/20661 | 11/1992 | WIPO |
| WO 94/13646 | 6/1994 | WIPO |
| WO 94/29309 | 12/1994 | WIPO |
| WO 96/10568 | 4/1996 | WIPO |
| WO96/34864 | 11/1996 | WIPO |
| WO 97/08166 | 3/1997 | WIPO |

OTHER PUBLICATIONS

*J. Med. Chem.*, 9 (1966), p. 181, Roderick et al..
Maggi et al, *Eur. J. Pharmacol.*, 166, (1989), p. 435–440.
Ellis et al, *J. Pharmacol. Exp. Ther.*, 267, 1 (1993), p. 95–101.
Furchgott, *Pharm. Rev.*, 7 (1955), p. 183–265.
Arunlakshana et al, *Brit. J. Pharmacol.*, 14, 48 (1959), p. 48–58.
Danko et al, *Pharmacol. Comm.*, 1, 3 (1992), p. 203–209.
Frossard et al., *Life Sciences* vol. 49, pp. 1941–1953 (1991).

*Primary Examiner*—Emily Bernhardt
*Attorney, Agent, or Firm*—Anita W. Magatti

[57] ABSTRACT

The invention relates to compounds of the formula

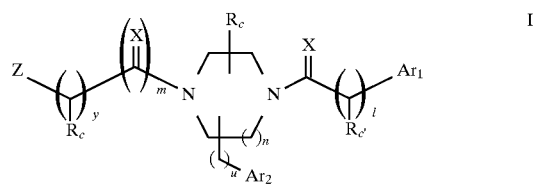

These compounds are neurokinin antagonists. These compounds are useful in the treatment of chronic airway diseases such as asthma.

1 Claim, No Drawings

PIPERAZINO DERIVATIVES AS NEUROKININ ANTAGONISTS

CROSS REFERENCE TO RELATED APPLICATIONS

This application is a continuation-in part of U.S. Ser. No. 08/663,880, filed Jun. 14, 1996, now U.S. Pat. No. 5,795,894 which is a continuation-in-part of International Application No. PCT/US96/05660, filed May 1, 1996, which claims the benefit of U.S. Provisional Application No. 60/003048, filed Aug. 31, 1995.

BACKGROUND OF THE INVENTION

The present invention relates to a genus of compounds useful as antagonists of neurokinin receptors. In particular, these can be neurokinin-1 receptor ($NK_1$) antagonists. Some can also be neurokinin-1 receptor ($NK_1$)antagonists and neurokinin-2 receptor ($NK_2$) antagonists, that is, $NK_1/NK_2$ dual receptor antagonists. Some can also be neurokinin-2 receptor ($NK_2$) antagonists. Some can also be neurokinin-3 receptor ($NK_3$) antagonists.

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example pulmonary disorders like asthma, cough, bronchospasm, chronic obstructive pulmonary diseases, and airway hyperreactivity; skin disorders and itch, for example, atopic dermatitis, and cutaneous wheal and flare; neurogenic inflammation inflammatory diseases such as arthritis, migraine, nociception; CNS diseases such as anxiety, Parkinson's disease, movement disorders and psychosis; convulsive disorders, renal disorders, urinary incontinence, ocular inflammation, inflammatory pain, and eating disorders such as food intake inhibition; allergic rhinitis, neurodegenerative disorders, psoriasis, Huntington's disease, depression, and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

Moreover, $NK_3$ receptor antagonists are especially useful in the treatment and prevention of asthma, inflammatory diseases and conditions, such as ocular inflammation, allergic rhinitis, cutaneous wheal and flare, psoriasis, atopic dermatitis, CNS diseases such as anxiety and Parkinson's disease.

SUMMARY OF THE INVENTION

The invention relates to compounds of the formula:

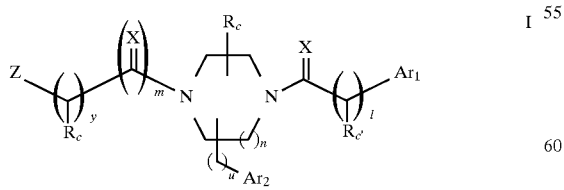

I each X is independently, O, (H,H), $NR_d$, or S;
n is 0 to 2; u is 0 to 2; l is 0 to 2;
m is 1, and y is 1 to 3; or m is 2, and y is 0;
each $R_c$ is independently H, $C_1$–$C_6$ alkyl, —$(CH_2)_{n_1}R_4$ where $n_1$ is 1 to 6; $R_d$ is independently selected from the group consisting of H, $C_1$–$C_6$ alkyl, CN, $OR_a$, phenyl, substituted phenyl, benzyl, substituted benzyl, or allyl, and with the further proviso that no more than one $R_c$ is other than H in the

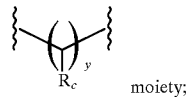

moiety;

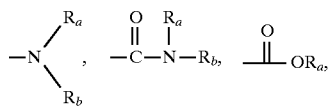

$R_4$ is —$OR_a$, $SR_a$,

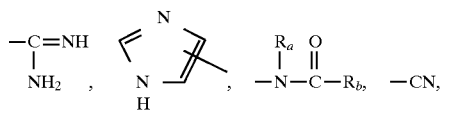

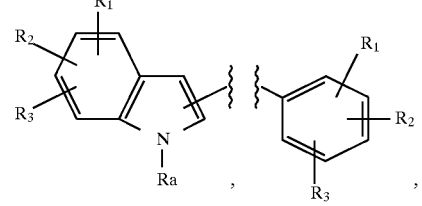

$R_c'$ is H, $C_1$–$C_6$ alkyl or $(CH_2)_nOR_a$, with the proviso that no more than one $R_c'$ is other than H;

each $R_a$ and $R_b$ is independently selected from the group consisting of H, $C_1$–$C_6$ alkyl, phenyl, substituted phenyl, benzyl, substituted benzyl, allyl; or when $R_a$ and $R_b$ are attached to the same nitrogen, then $R_a$ and $R_b$ together with the nitrogen to which they are attached, form a 4 to 7 member ring;

wherein each $R_1$ and $R_2$ is independently H, $C_1$–$C_6$ alkyl, $CF_3$, $C_2F_5$, Cl, Br, I, F, $NO_2$, $OR_a$, CN, $NR_aR_b$,

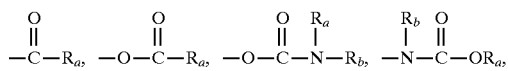

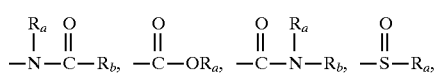

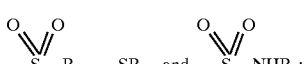

and where $R_a$ is not H in

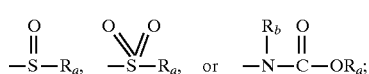

or when $R_1$ and $R_2$ are on adjacent carbons on a ring, they can form

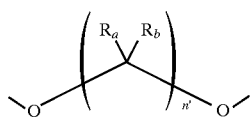

wherein n' is 1 or 2;

and each $R_3$ is independently H, $C_1$–$C_6$ alkyl, $CF_3$, $C_2F_5$,

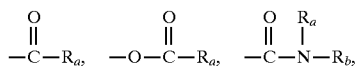

Cl, Br, I, F, $OR_a$, $OCF_3$ or phenyl;

$Ar_1$ is heteroaryl or substituted heteroaryl,

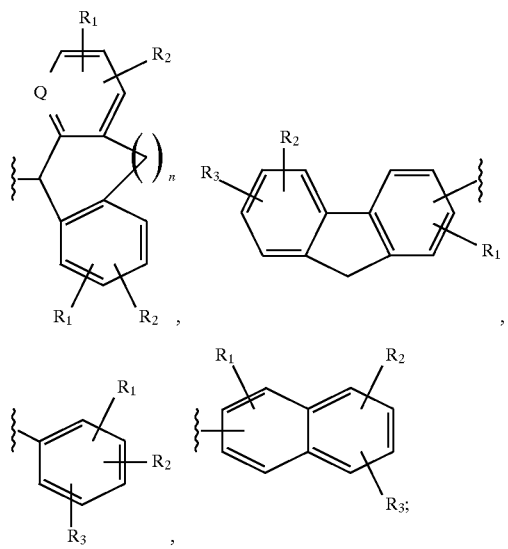

or

Q is N or CH;

$Ar_2$ is heteroaryl, substituted heteroaryl,

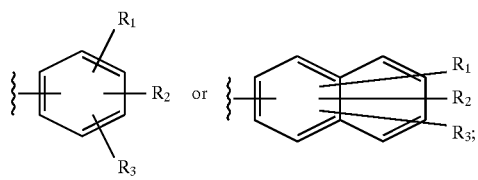

Z is

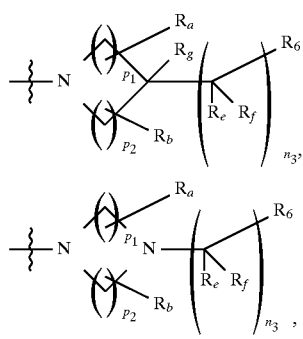

or

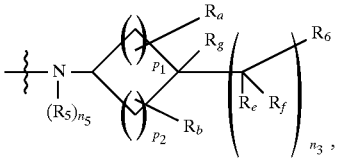

wherein $p_1$ and $p_2$ are each independently 1 to 4 with the proviso that $p_1$ and $p_2$ added together are 2 to 6; $n_5$ is 1 to 2;

each $R_5$ is independently selected from the group consisting of H, OH,

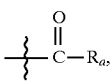

$C_1$–$C_6$ alkyl, —$(CH_2)_{n_1}R_4$ where $n_1$ is 1 to 6 with the proviso that when $n_1$ is 1, $R_4$ is not OH or $NR_aR_b$; also with the proviso that when $n_5$ is 2, $R_5$ is $C_1$–$C_6$ alkyl, and two $R_5$ can be attached to the nitrogen to form a quaternary salt;

each $R_a$ and $R_b$ is independently selected from the group consisting of H, $C_1$–$C_6$ alkyl, phenyl, substituted phenyl, benzyl, substituted benzyl, allyl;

$n_3$ is 0–4; each $R_e$ and $R_f$ is independently selected from the group consisting of H, $C_1$–$C_6$ alkyl, phenyl, substituted phenyl, benzyl, substituted benzyl, allyl; or $R_e$ and $R_f$ taken together with the carbon to which they are attached can also form a carbonyl group with the proviso that no more than one carbonyl group is in the

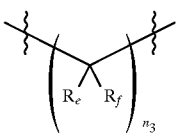

moiety.

$R_g$ is hydrogen

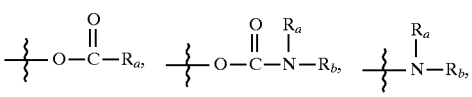

$R_6$ is H, $C_1$–$C_6$ alkyl, allyl, $C_3$–$C_6$ cycloalkyl,

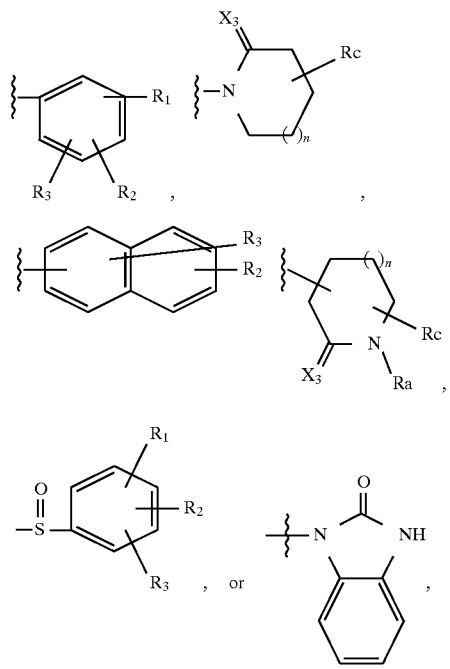

wherein $X_3$ is O, (H,H), $NR_d$, or S; or $R_6$ is heteroaryl, substituted heteroaryl, heterocycloalkyl, substituted heterocycloalkyl, when $n_3$ is 0–4;

or when $R_e$, $R_f$ taken together with the carbon atom to which they are attached form a carbonyl group and $n_3$ is 1, $R_6$ can also be $OR_a$ wherein $R_a$ is not H, and $R_6$ can also be -($NR_a,R_b$), O-heteroaryl, O-substituted heteroaryl, O-heterocycloalkyl, O-substituted heterocycloalkyl, -$NR_a$-heteroaryl, -$NR_a$-substituted heteroaryl, -$NR_a$-heterocycloalkyl, -$NR_a$-substituted heterocycloalkyl.

or a pharmaceutically acceptable salt thereof.

All of the variables in the above formulas such as Z, $R_1$, $R_2$, and $R_3$, have the same meaning throughout the specification unless otherwise specified.

Preferred compounds of the invention are compounds of formula I, wherein each X is O or (H,H) and at least one X is O.

Also preferred are compounds of formula I wherein both X's are O.

Also preferred are compounds of formula I wherein l is 0, m is 1, and y is 1–3.

Also preferred are compounds of formula I wherein n is 1 and u is 0.

Also preferred are compounds of formula I wherein $Ar_1$ is

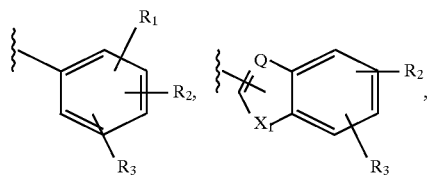

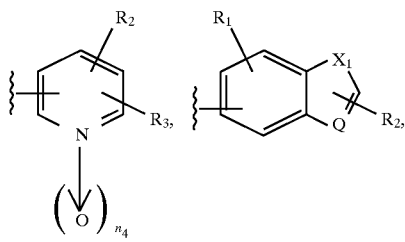

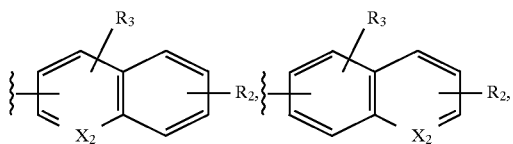

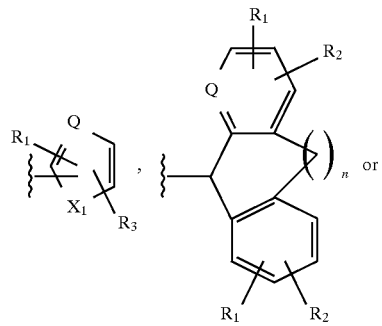

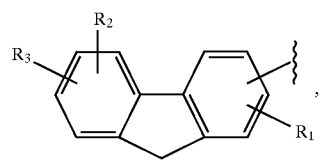

wherein Q is N or CH;

each $X_1$ is independently O, S or $NR_a$;

each $X_2$ is independently CH or N; and $n_4$ is 0 or 1.

Also preferred are compounds of formula I wherein $Ar_2$ is

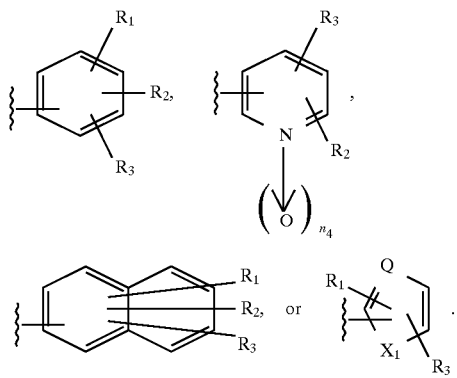

Also preferred are compounds of formula I wherein Z is

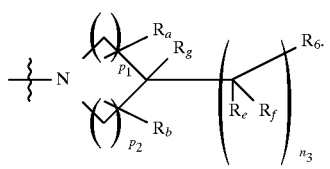

Also preferred are compounds of formula I wherein Z is

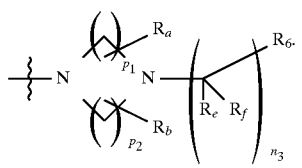

Also preferred are compounds of formula I wherein Z is

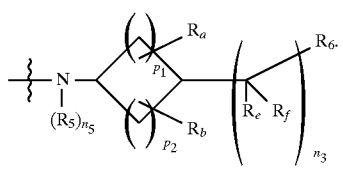

In the rings above, one $R_a$ and one $R_b$ can be present at any position on the ring which will allow for a substitution Also preferred are compounds of formula II

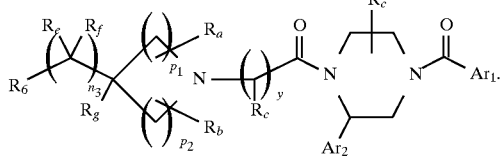

wherein $R_c$ is H; y is 1–3; $p_1$ and $p_2$ are 2; $R_e$, $R_f$ are H, $C_1$–$C_6$ alkyl, $C_3$–$C_6$ cycloalkyl, allyl; $n_3$ is 0–4; $Ar_1$ and $Ar_2$ are both

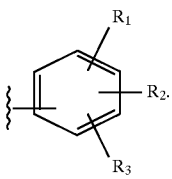

Also preferred are compounds of formula II wherein $R_6$ is

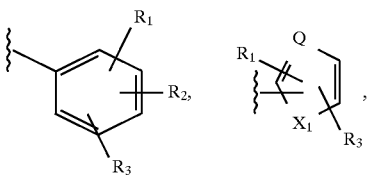

-continued

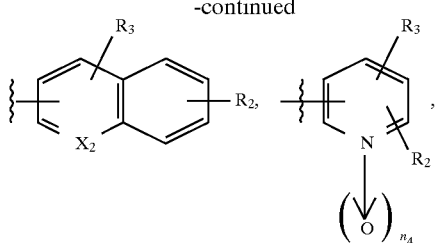

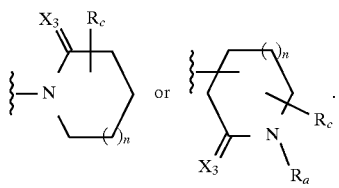

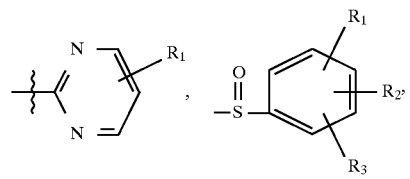

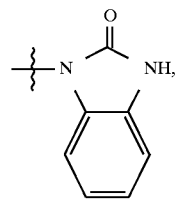

or $R_e$, $R_f$ taken together with the carbon to which they are attached form a carbonyl group, $n_3$ is 1 and $R_6$ is

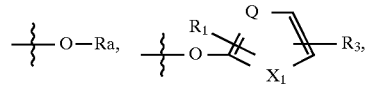

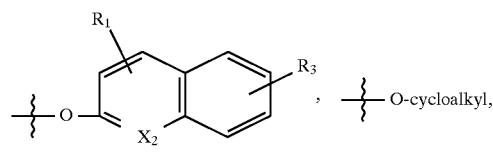

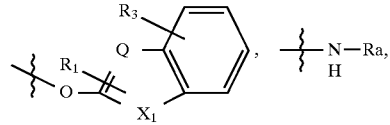

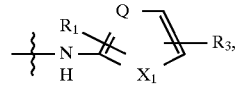

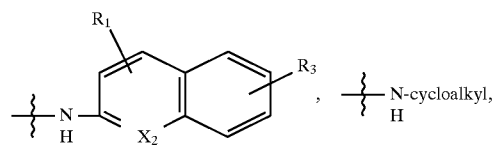

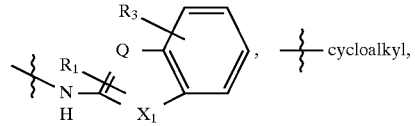

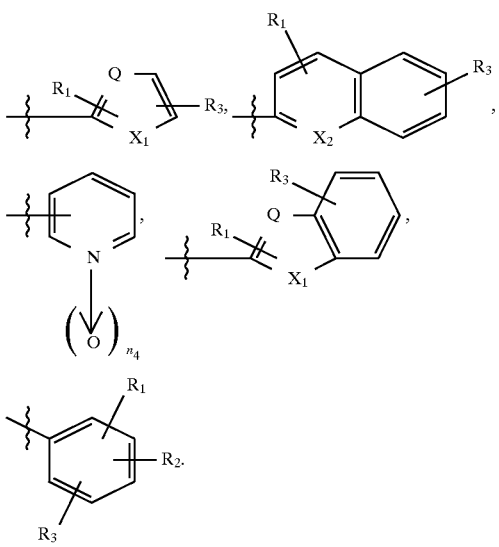

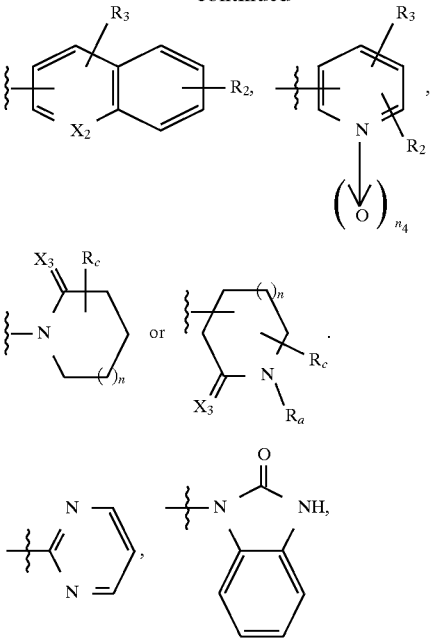

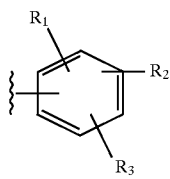

Also preferred are compounds of formula II wherein $R_6$ is

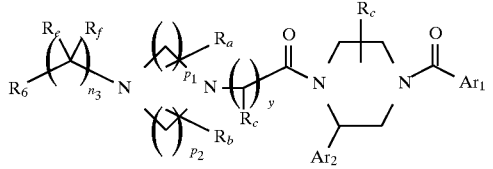

Also preferred are compounds of formula III

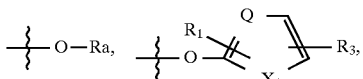

III wherein $R_c$ is H; y is 1–3; $p_1$ and $p_2$ are 2; $R_e$, $R_f$ are H, $C_1$–$C_6$ alkyl, $C_3$–$C_6$ cycloalkyl, allyl; $n_3$ is 0–4; $Ar_1$ and $Ar_2$ are both

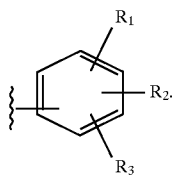

Also preferred are compounds of formula III wherein $R_6$ is

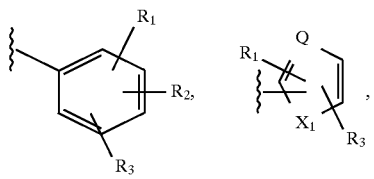

or $R_e$, $R_f$ taken together with the carbon to which they are attached form a carbonyl group, $n_3$ is 1, and $R_6$ is

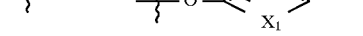

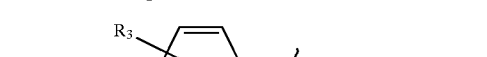

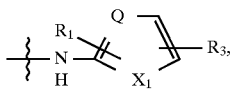

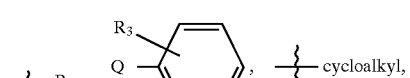

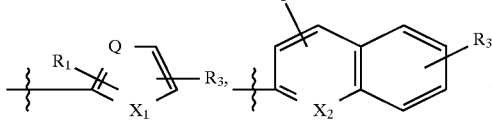

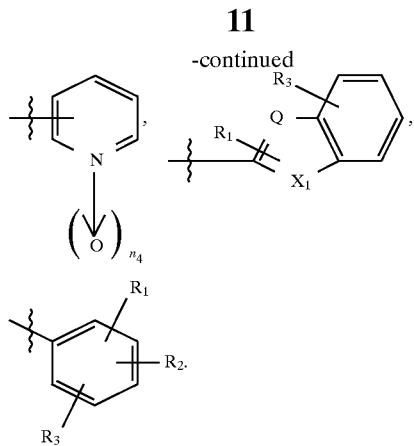

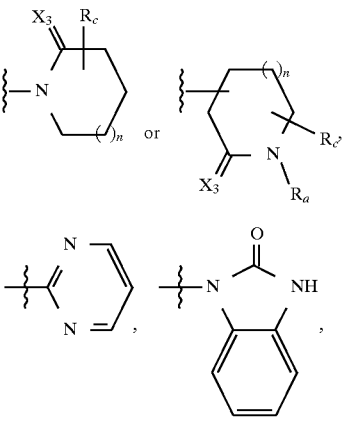

Also preferred are compounds of formula III wherein $R_6$ is

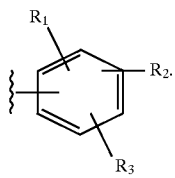

Also preferred are compounds of formula IV

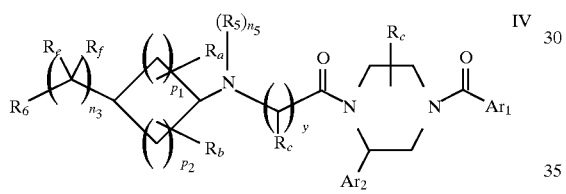

wherein $R_c$ is H; y is 1–3; $p_1$, $p_2$ are 1–2; $R_e$, $R_f$ are H, $C_1$–$C_6$ alkyl, $C_3$–$C_6$ cycloalkyl, allyl; $n_3$ is 0–4; $Ar_1$ and $Ar_2$ are both

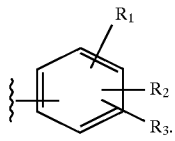

Also preferred are compounds of formula IV wherein $R_6$ is

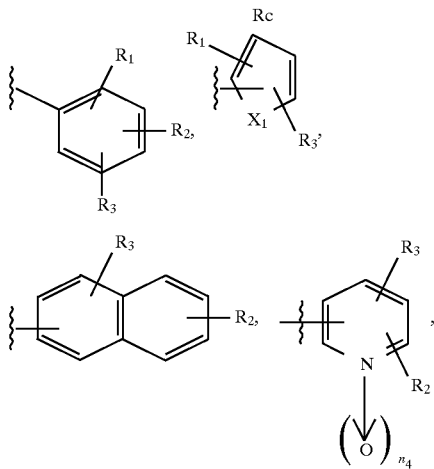

or $R_e$, $R_f$ taken together with the carbon to which they are attached form a carbonyl group, $n_3$ is 1, and $R_6$ is

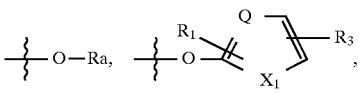

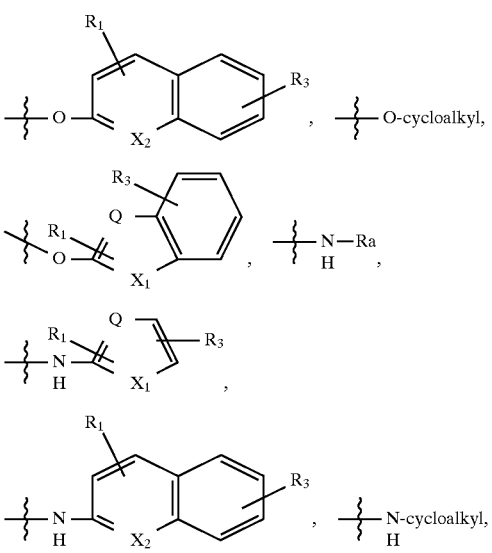

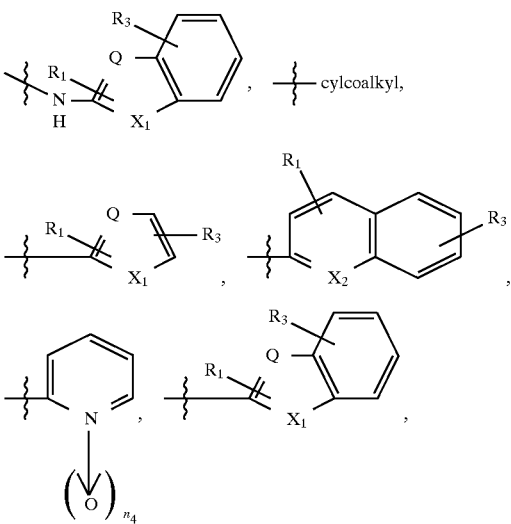

-continued
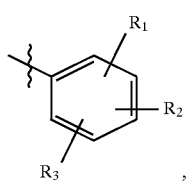
Also preferred are compounds of formula IV wherein $R_6$ is
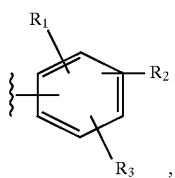
Exemplary compounds of the invention are compounds of the formulas:
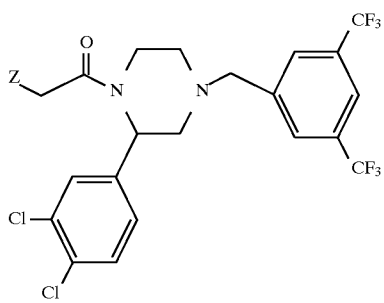
Where Z is
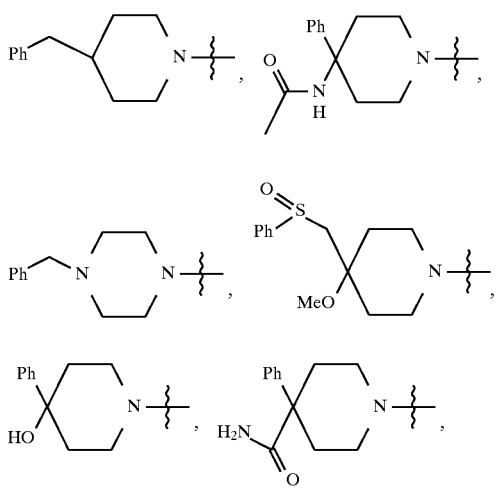
or a compound selected from the group consisting of
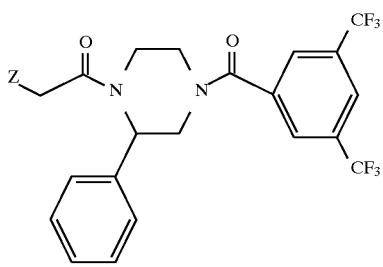
Where Z is
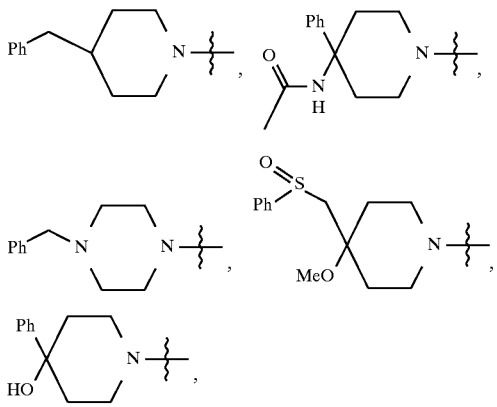
or a compound selected from the group consisting of
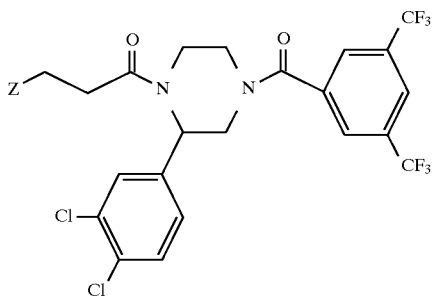
Where Z is
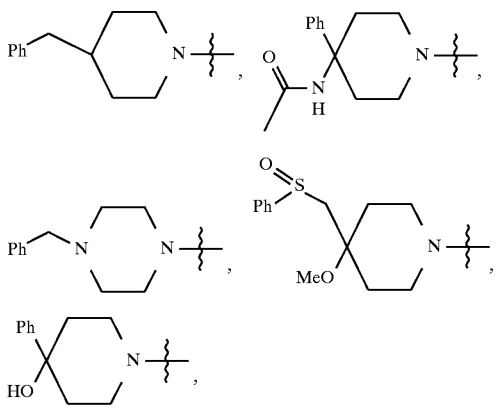

or a compound selected from the group consisting of
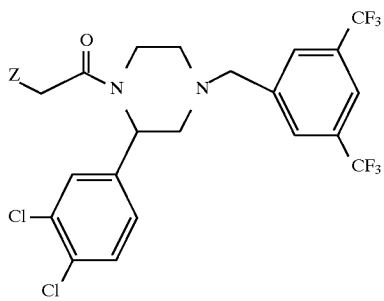
Where Z is
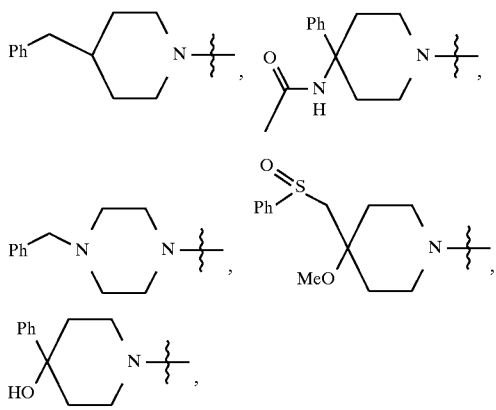
or a compound selected from the group consisting of
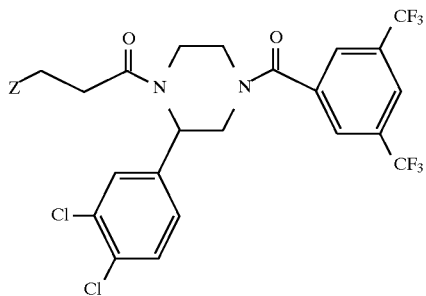
Where Z is
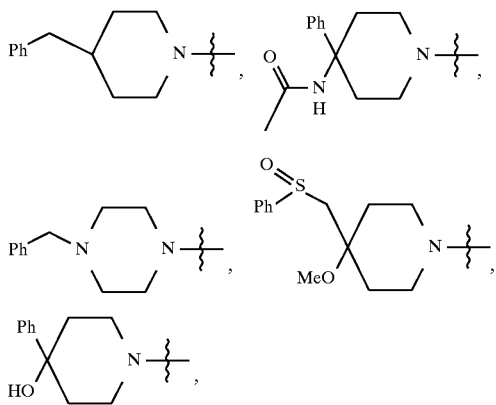
or a compound selected from the group consisting of
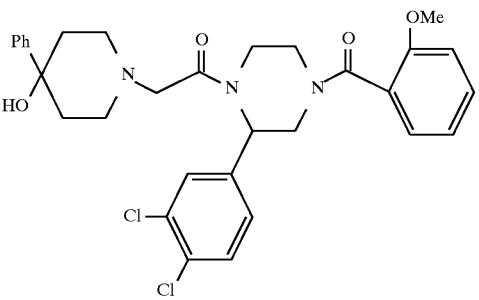
or a compound selected from the group consisting of
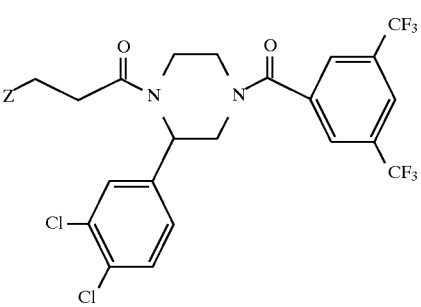
Where Z is
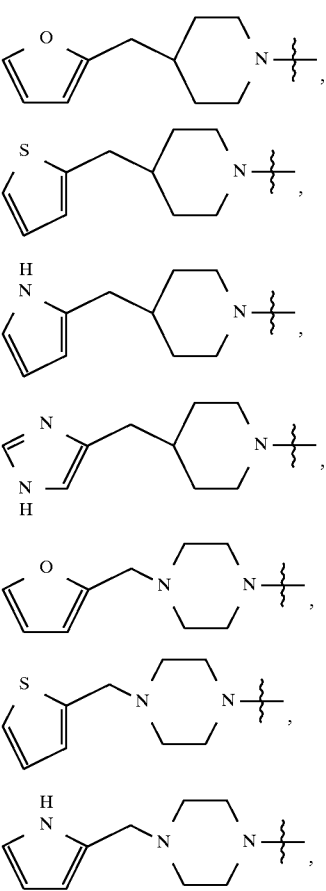

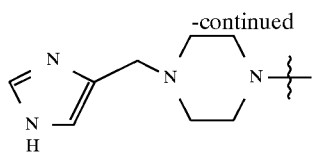
or a compound selected from the group consisting of
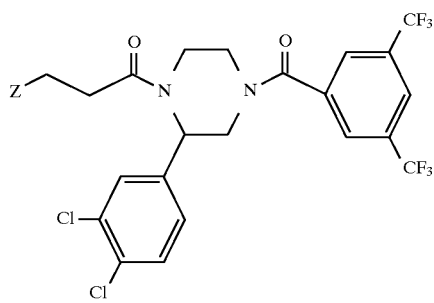
Where Z is
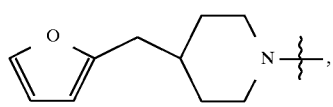
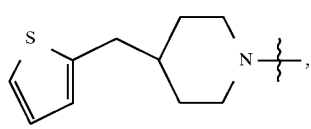
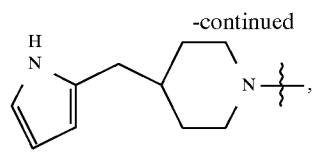
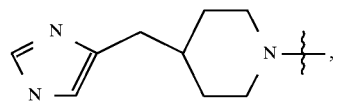
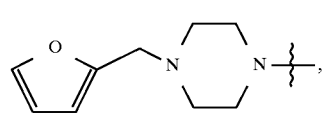
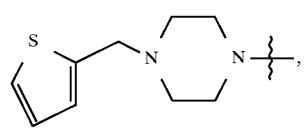
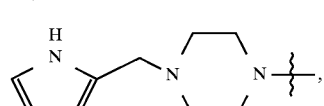
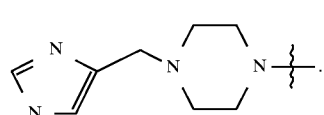
or a compound selected from the group consisting of
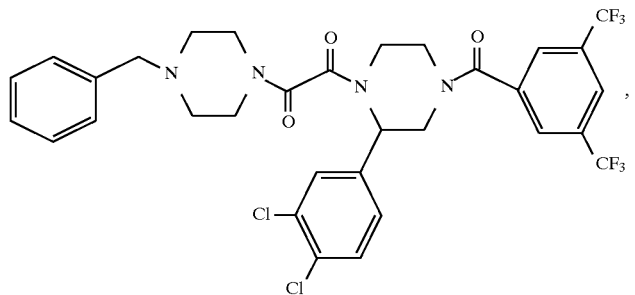
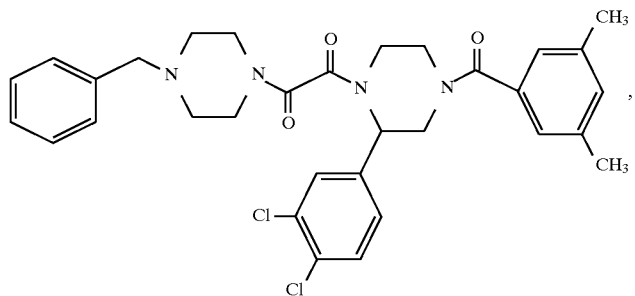

-continued
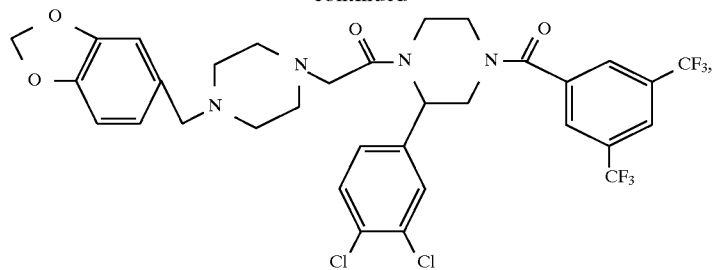
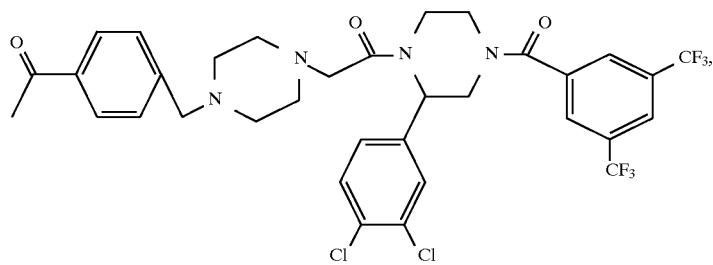
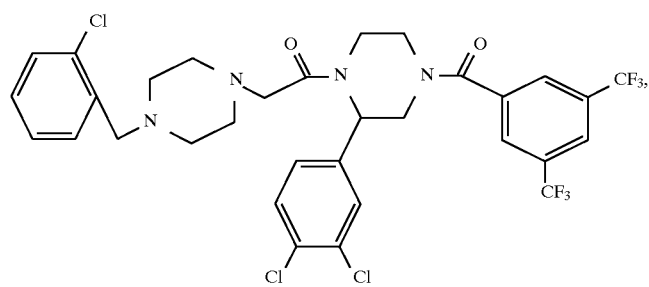
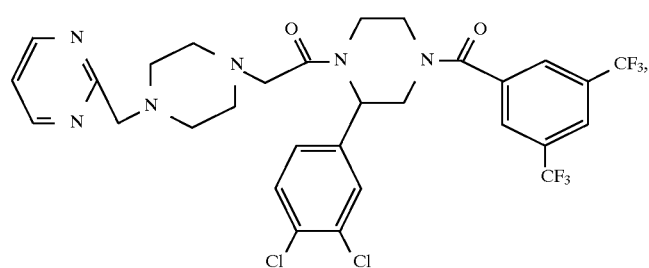
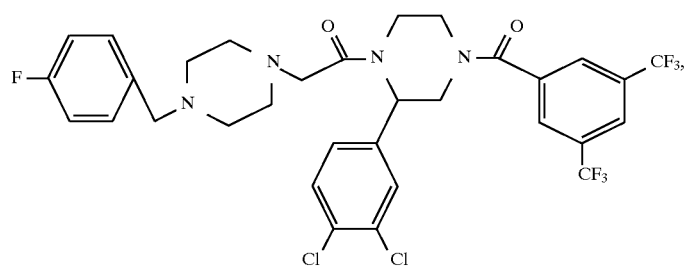
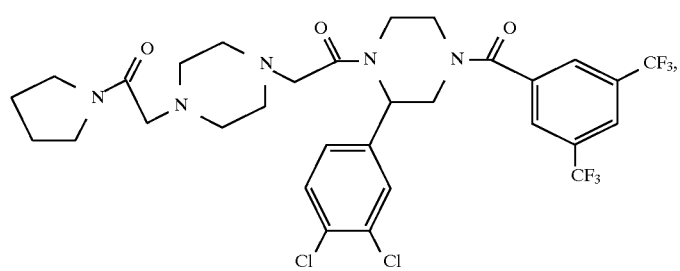

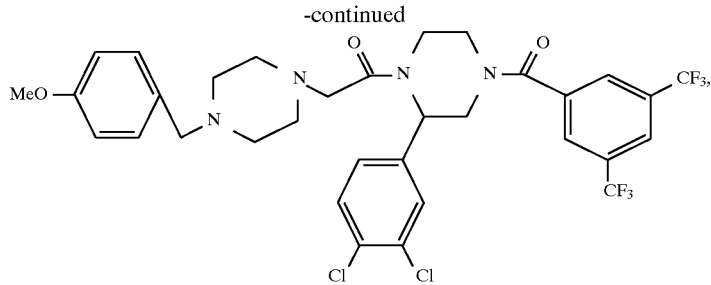
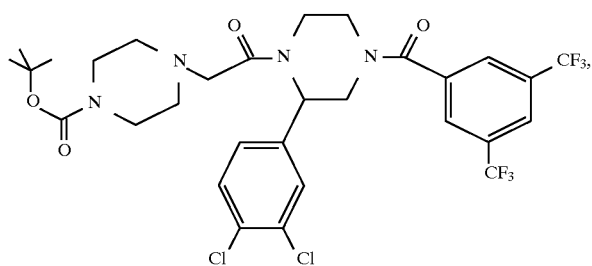
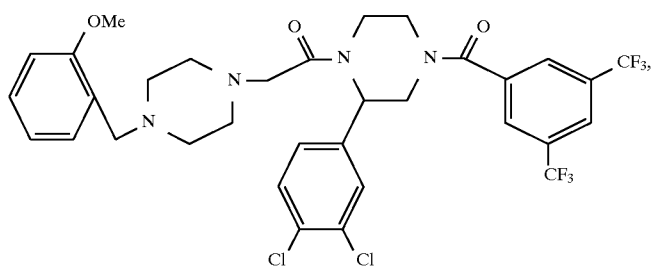
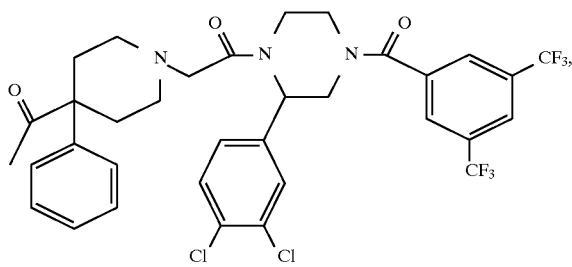
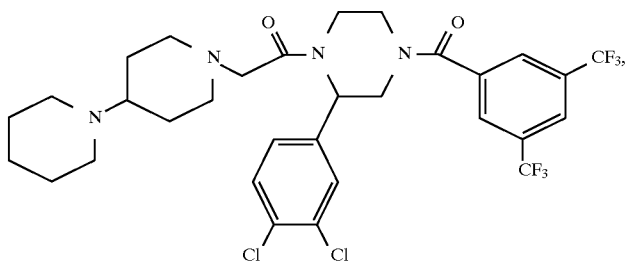
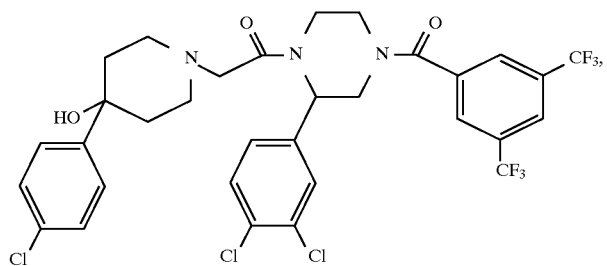

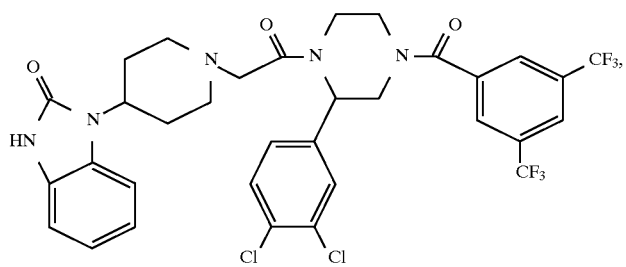
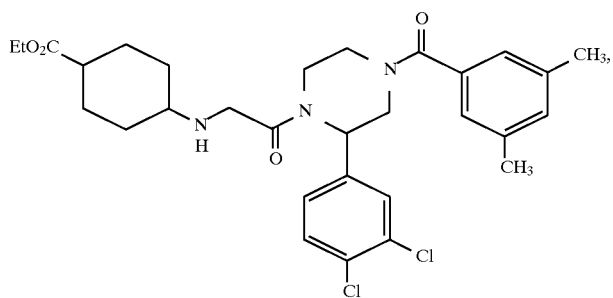
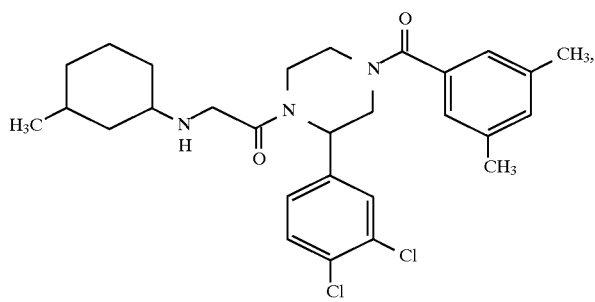
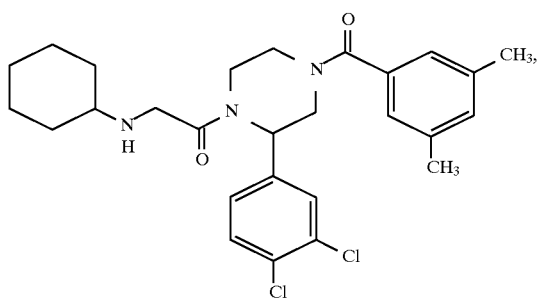
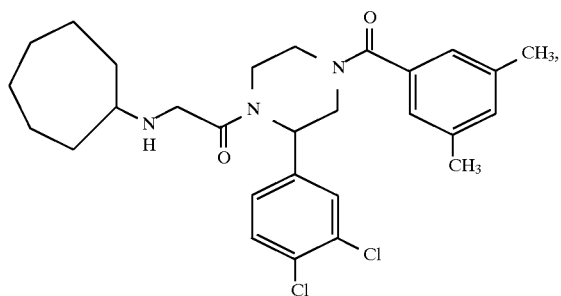

-continued
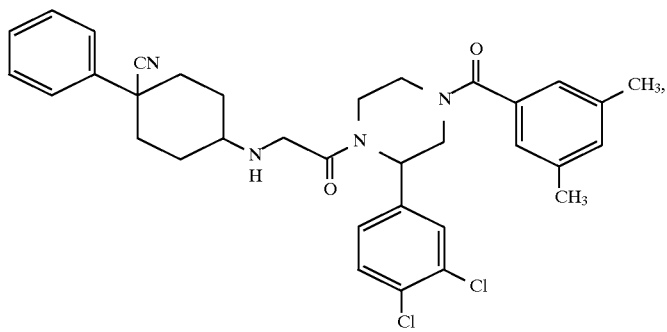
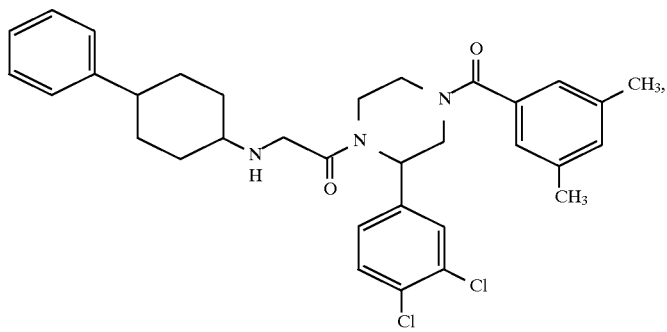
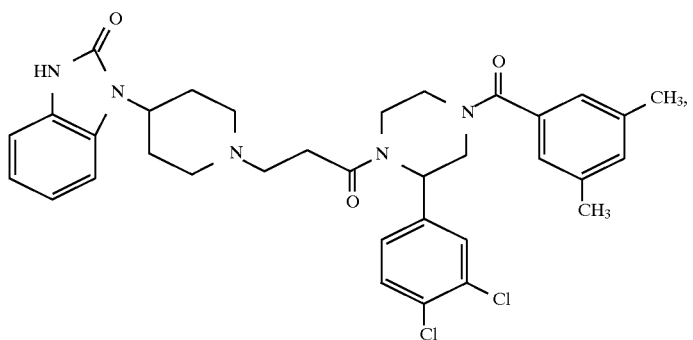
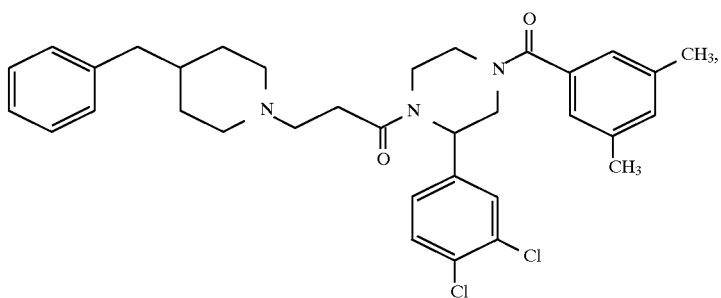
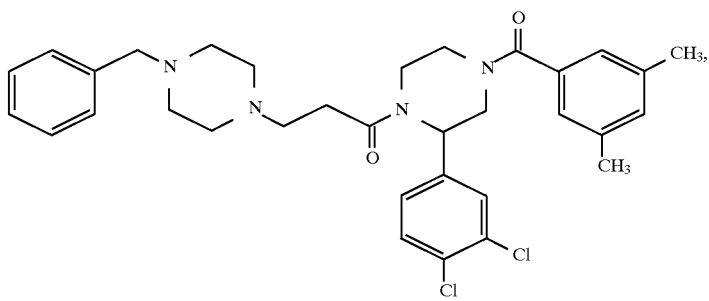

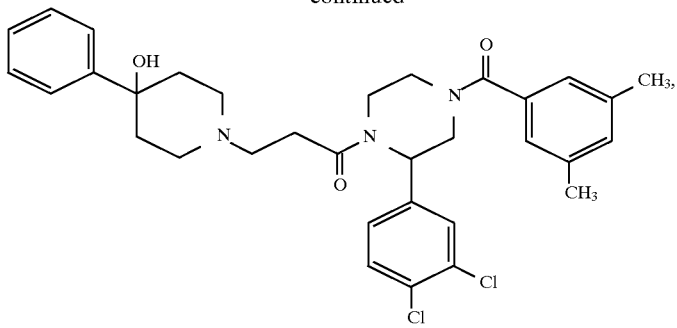

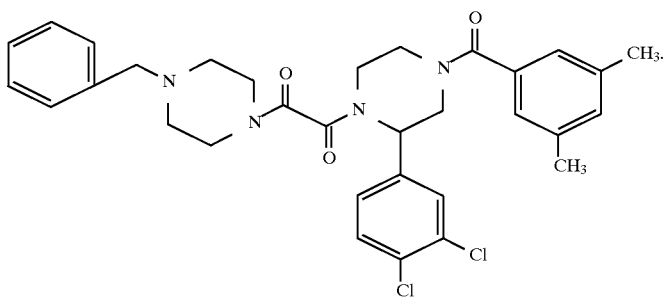

or a pharmaceutically acceptable salt thereof.

The invention also relates to a pharmaceutical composition comprising a thereapeutically effective amount of a compound of formula I in combination with a pharmaceutically acceptable carrier.

The invention also relates to a method for inducing neurokinin antagonism which comprises administering a neurokinin antagonistic effective amount of a compound of formula I to a mammal in need thereof.

The invention also relates to a method for treating chronic airway diseases such as asthma and allergies; inflammatory diseases such as inflammatory bowel disease, psoriasis, fibrositos, osteoarthritis, and rheumatoid arthritis; migraine; central nervous system disorders such as depression, psychosis, dementia, and Alzheimer's disease; Down's syndrome; neuropathy; multiple sclerosis; ophthalmic disorders; conjunctivitis; auto immune disorders; graft rejection; systemic lupus erythematosus; GI disorders such as Crohn's disease and ulcerative colitis; disorders of bladder function; circulatory disorders such as angina; Raynaud's disease; coughing and pain. In particular, the invention also relates to a method of treating asthma which comprises administering to a mammal in need of such treatment an anti-asthma effective amount of a compound of formula I for such purpose.

DETAILED DESCRIPTION OF THE INVENTION

As used herein the term alkyl means a straight or branched, saturated hydrocarbon chain having from 1 to 6 carbon atoms. The number of carbon atoms may be designated. For example, "$C_1$–$C_6$ alkyl" represents a straight or branched, saturated hydrocarbon having from 1 to 6 carbon atoms.

The term $C_3$–$C_6$ cycloalkyl means a cycloalkyl having from 3 to 6 carbon atoms, that is cyclopropyl, cyclobutyl, cyclopentyl and cyclohexyl.

The term alkenyl means means a straight or branched, saturated alkenyl having from 2 to 6 carbon atoms. The number of carbon atoms may be designated. For example, "$C_2$–$C_6$ alkenyl" represents a straight or branched alkenyl having from 1 to 6 carbon atoms.

The term alkynyl means a straight or branched alkynyl having from 2 to 6 carbon atoms. The number of carbon atoms may be designated. For example, "$C_2$–$C_6$ alkynyl" represents a straight or branched chain alkynyl having from 2 to 6 carbon atoms.

As used herein, a heavy dark line (━) denotes a chemical bond coming above the plane of the page. A dashed line (⋯) denotes a chemical bond coming below the plane of the page.

As used herein,

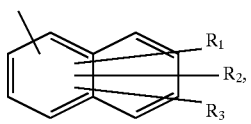

for example, means that $R_1$, $R_2$, and $R_3$ can be in either of the rings of the above naphthyl moiety.

In the rings shown below, one $R_a$ and one $R_b$ can be present at any position on the ring which will allow for a substitution:

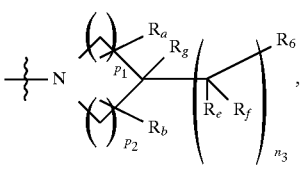

-continued

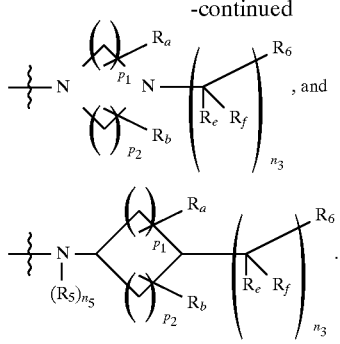

Similarly, in the rings shown below, one $R_c$ can be present at any position on the ring which will allow for a substitution:

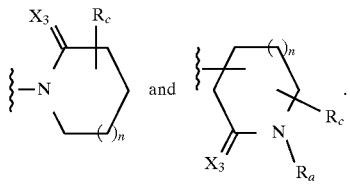

Asymmetric centers exist in compounds of formula I of the invention. Accordingly, compounds of formula I include stereoisomers.

All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization, preparative plate or column chromatography on silica, alumina, or reversed phase supports or HPLC (high performance liquid chromatography).

Enantiomers may be separated, where appropriate, by derivatization or salt formation with an optically pure reagent, followed by separation by one of the aforementioned methods. Alternatively, enantiomers may be separated by chromatography on a chiral support.

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

Those compounds of formula I which contain a basic group such as —$CH_2NH_2$, form pharmaceutically acceptable salts. The preferred pharmaceutically acceptable salts are nontoxic acid addition salts formed by adding to a suitable compound of the invention about a stoichiometric amount of a mineral acid, such as HCl, HBr, $H_2SO_4$ or $H_3PO_4$ or of an organic acid such as acetic, propionic, valeric, oleic, palmitic, stearic, lauric, benzoic, lactic, para-toluenesulfonic, methanesulfonic, citric, maleic, fumaric, succinic and the like, respectively.

General Methods of Preparation

The compounds of this invention may be prepared by one of the following general methods. As used herein RT means room temperature. Unless otherwise indicated, variables in the structural formulas below are as defined above. Starting materials and reagents used in the methods and examples below, are known or may be prepared according to known methods.

As used herein the term "substituted phenyl" means

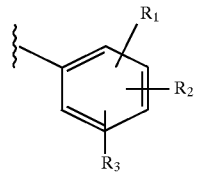

wherein $R_1$, $R_2$, and $R_3$ are as described herein.

"substituted" means substituted by $R_1$, $R_2$, and/or $R_3$ as described herein.

"Aryl" means phenyl, naphthyl, indenyl, tetrahydronaphthyl, indanyl, anthracenyl or fluorenyl.

"Halogeno" refers to fluoro, chloro, bromo or iodo atoms.

"Heterocycloalkyl" refers to 4- to 6-membered rings comprising 1 to 3 heteroatoms independently selected from the group consisting of —O—, —S— and —N($R^6$)—, with the remaining ring members being carbon. Examples of heterocycloalkyl rings are tetrahydrofuranyl, pyrrolidinyl, piperidinyl, morpholinyl, thiomorpholinyl and piperazinyl.

"Heteroaryl" refers to 5- to 10-membered single or benzofused aromatic rings comprising 1 to 3 heteroatoms independently selected from the group consisting of —O—, —S— and —N=. Examples of single-ring heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. Examples of benzofused heteroaryl groups are quinolinyl, thianaphthenyl and benzofurazanyl. N-oxides of nitrogen-containing heteroaryl groups are also included. All positional isomers are contemplated, e.g., 1-pyridyl, 2-pyridyl, 3-pyridyl and 4-pyridyl.

Where $R^2$ and $R^3$ substituents form a ring and additional heteroatoms are present, the rings do not include adjacent oxygen and/or sulfur atoms or three adjacent heteroatoms. Typical rings so formed are morpholinyl, piperazinyl and piperidinyl.

As used herein, the term "BOC" means t-butoxycarbonyl.

As used herein, the term "Ph" means phenyl.

As used herein, the term "RT" means room temperature.

As used herein, the term "parallel synthesis" means the preparation of individual chemical compounds as one of a batch of, for instance, 20, 30, or even 100 identical reactions on usually a single substrate but using a different reagent in each vessel. Such reagents are always of the same general class—in this case, either carboxylic acids or organic amines in any set of parallel reactions. The conditions used for each reaction are identical to those described in the examples, except that a simplified work-up is employed, generally a simple wash either with acid or base if appropriate, then water. The presence of the product is detected by thin layer chromatography (TLC) using known products as representative standards. Further characterization by combination HPLC/MS is generally performed. No further purification is performed on these materials before they are submitted to biological assays.

As used herein, each $R_c$ and $R_c'$ is independently selected from the group consisting of H, $C_1$–$C_6$ alkyl, $C_2$–$C_6$ alkenyl, $C_2$–$C_6$ alkynyl, unsubstituted or substituted phenyl, and unsubstituted or substituted benzyl, The starting materials in the methods below are either known or can be prepared in accordance with known methods. In particular, the following compounds are either known or can be prepared in accordance with known methods: the diamine A, the compounds of formulas A, VI, VIII, X, XI, XIV, XVIII, XIX, XXa, A', XXV, and Z-H, as well as esters of formula XI, and compounds of formula

Method 1. If the group $Ar_2$ is an aromatic group with no I or Br substituents, then the following method may be used to prepare the useful intermediates (IV):

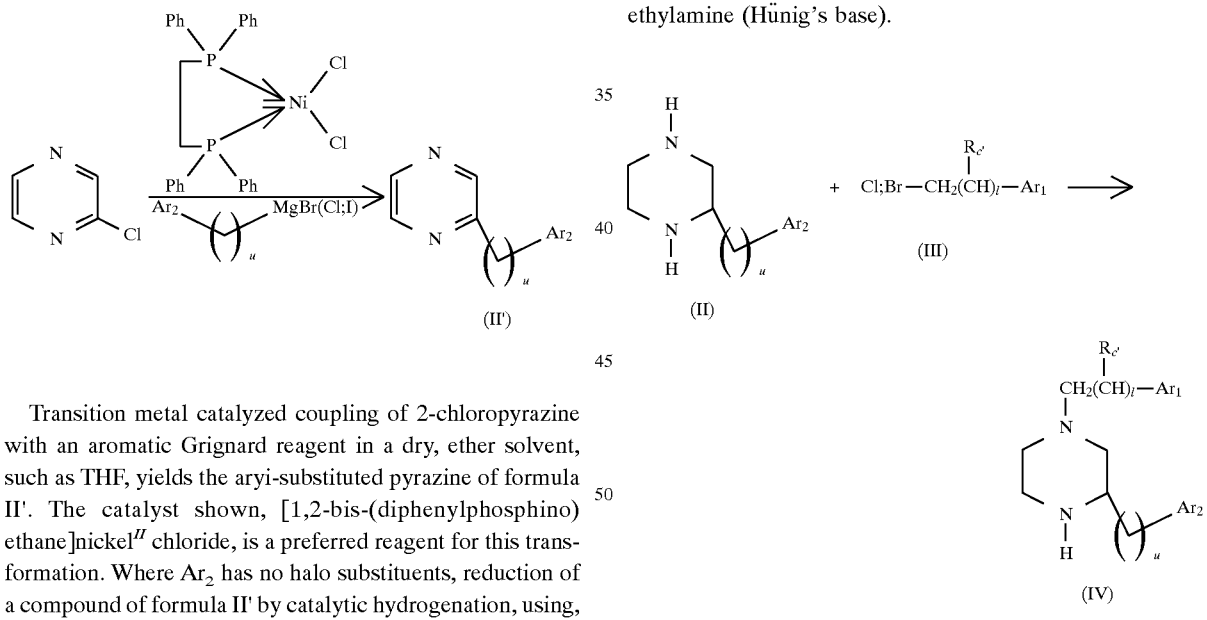

Transition metal catalyzed coupling of 2-chloropyrazine with an aromatic Grignard reagent in a dry, ether solvent, such as THF, yields the aryl-substituted pyrazine of formula II'. The catalyst shown, [1,2-bis-(diphenylphosphino) ethane]nickel$^{II}$ chloride, is a preferred reagent for this transformation. Where $Ar_2$ has no halo substituents, reduction of a compound of formula II' by catalytic hydrogenation, using, for instance, palladium acetate, preferably in acetic acid solvent, results in preferential reduction of the pyrazine ring, leaving the aromatic ring unreduced, that is, it results in a compound of formula II. Similarly, 10% Pd on charcoal (Pd-C) can be used in an alcohol solvent, preferably methanol, with or without the addition of a small quantity (1 to 5 equivalents) of acetic acid. Reaction times of about 1 to 24 hours generally suffice for this reaction, which is preferentially run at room temperature or slightly above (up to about 50° C.) and using from 1 to about 6 atmospheres pressure of hydrogen.

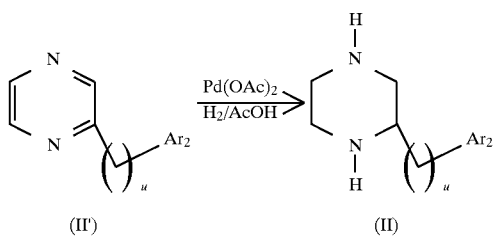

The intermediate of formula II may also be prepared from a compound of formula II', even if the group $Ar_2$ contains halogen atoms, by reduction using a strong hydride ion donor, preferably lithium aluminum hydride (LAH) or diisobutyl aluminum hydride (DIBAL-H) in an ether solvent, such as ether, THF or dimethoxyethane (DME).

Selective alkylation of a compound of formula II is possible using low temperature conditions. Thus, reacting a compound of formula II with a substituted aryl-alkyl halide of formula III where l is 0 to 2, results in the formation of the 4-substituted derivative of formula IV. Suitable conditions include use of a halogenated solvent, such as $CH_2Cl_2$, at low temperature. Suitable temperatures are from −78° C. initially, allowing the reaction mixture to warm gradually to RT if the reaction is not completed after several hours. The reaction is catalyzed by the addition of an equivalent amount of an organic base, such as triethylamine and diisopropylethylamine (Hünig's base).

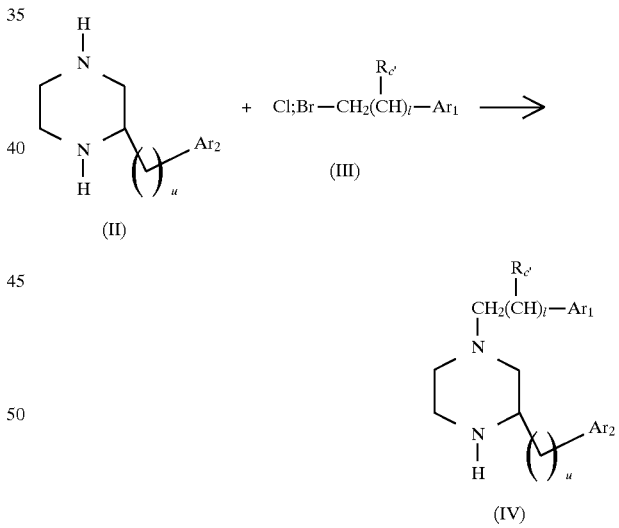

Method 2. If the group $Ar_2$ contains one or more halogen atoms on an aromatic ring and the other groups are as in Method 1, then an alternate route to a compound of formula IV is preferred. In addition, this method can be used to prepare compounds in which l is from 0 to 2. Monoprotection of the diamine of formula (A), preferably with BOC anhydride, or other agents known to introduce the t-butyloxycarbonyl protecting group, in an alcohol solvent, such as methanol, preferably at about −10° C., produces a compound of formula V.

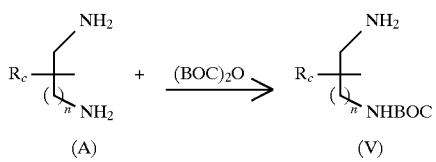

These compounds are used to perform a reductive amination reaction with the aldehyde of formula VI to produce an amine of formula VII. (In structures (A), (V), (VII), and (IX) herein, $R_c$ can be bound to any position between the two nitrogens. In cyclic structures like (IVA) below, $R_c$ can be bound to any available cyclic position that is occupied by carbon, and that is between the two nitrogens.)

Suitable conditions for this type of reaction include the use of an alcohol solvent, preferably methanol, or 2,2,2-trifluoroethanol, made slightly acidic with a weak organic acid, such as acetic acid, and a reducing agent known to favor reductive amination reactions, preferably sodium cyanoborohydride, $NaBH_3CN$.

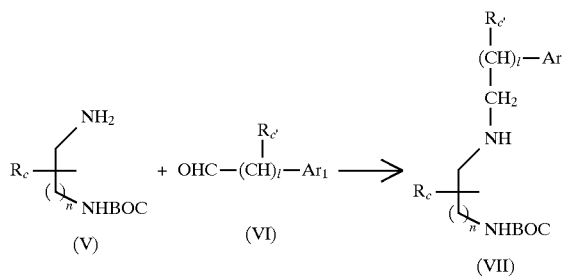

Reaction of a compound of formula VII with an α-haloketone of formula VIII, in which $Ar_2$ preferably represents a halogenated aromatic ring, but may be any of the claimed aromatic rings, in the presence of an organic base, such as di-isopropylethylamine, also known as Hünig's Base, in an ether solvent, such as THF, results in the formation of the intermediates of formula IX.

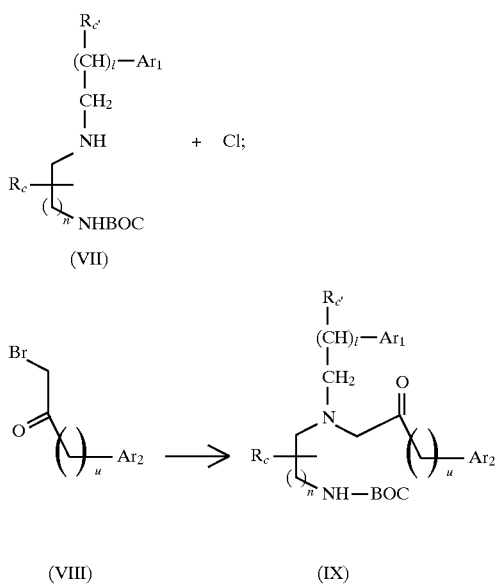

Removal of the BOC protecting group using a suitable acidic catalyst, such as trifluoroacetic acid, followed by an intramolecular reductive amination, under conditions such as those described above for the preparation of a compound of formula VII, leads to the formation of compounds of formula IVA.

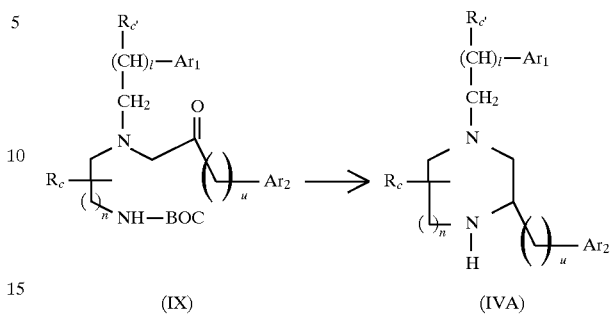

Method 3. An alternate route to compounds of the invention in which l is 0 to 2 is as follows. Standard coupling of an N-protected amino acid of formula X, wherein $Ar_2$ is as described above, with an amino acid ester derivative

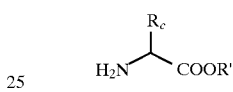

(R' is $C_2$–$C_4$ alkyl, preferably, the ethyl ester of formula XI, .Et in the formulas herein means ethyl), produces a dipeptide of formula XII. A suitable protecting group is BOC, although many others may also be used. Other esters of the amino acid may also be used. Standard coupling techniques may be applied, an example being the use of N-hydroxybenztriazole (HOBT) and a water-soluble carbodiimide, such as 1-(3-dimethylaminopropyl)-3-ethylcarbodiimide (DEC), in a non-hydroxylic solvent such as $CH_2Cl_2$, DMF or a mixture of the two foregoing solvents. The reaction is run, preferably, at or below RT, and takes from 1 to 40 hours for completion, depending upon the substrates.

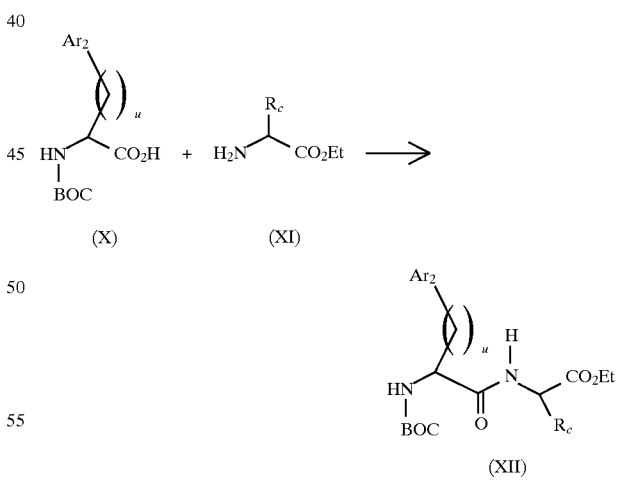

Removal of the protecting group under standard conditions, followed by treatment of the product with a base results in cyclization to the diketopiperazine of formula XIII. Suitable conditions for removal of the exemplified BOC group are well known in the art and include catalysis by trifluoroacetic acid (TFA). A suitable base for cyclization is the alkali metal salt of an alcohol in the alcohol itself used as solvent. For example, a solution of sodium ethoxide in ethanol may be used. The temperature is preferably around RT but may be slightly above or below, in the range 0° C. to about 40° C. The reaction is generally complete within a few hours. Suitable reaction times are from 1 to 24 hours.

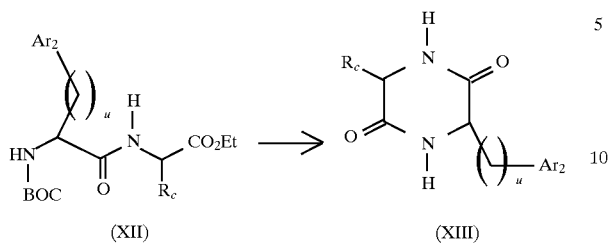

Reduction of the diketopiperazine of formula XIII to a compound of formula II may be accomplished preferentially with a strong hydride reducing agent, such as LAH or a solution of sodium bis(2-methoxyethoxy)aluminum hydride in toluene (also known as Red-Al®), or the $BH_3 \cdot S(CH_3)_2$ complex. Suitable solvents for this reaction are DME and other higher boiling ethers since the reaction is run at elevated temperatures, from about 50° C. to about 110° C., preferably at about 90° C.

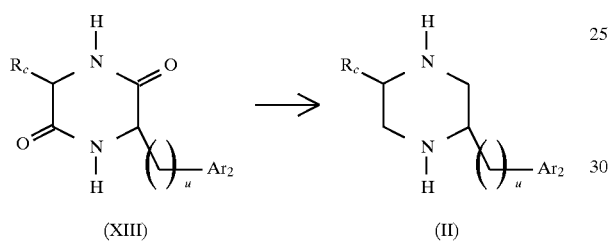

Alternatively, a compound of formula of II may be prepared by the scheme shown below (J. Med. Chem., 9, 181 (1966)). As used herein L is any readily available ester residue such as $C_1$–$C_7$ alkyl, more preferably methyl or ethyl.

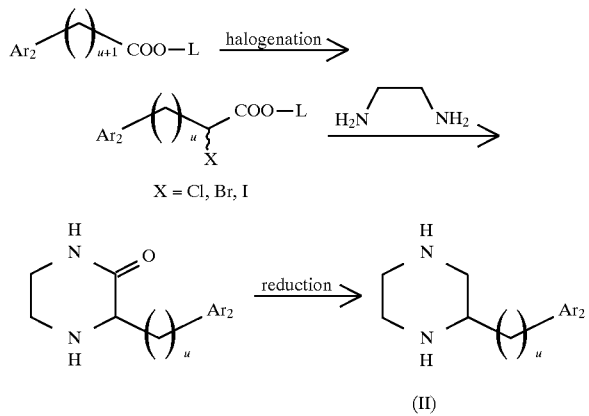

A compound of formula II may be converted to a compound of formula IV by the processes described in Method 1 above or Method 6 below.

Method 4. The intermediates of formula IV or IVA, formed via any of the previous methods, may be further processed as follows. A compound of formula IVA will be used in the Schemes. Reaction of a compound of formula IVA with an activated halo-acid, generally the acid halide of formula XIV, in which Hal represents Cl, Br, or I, yields the acylated derivative of formula XV that is, m is 1 for formula I. An organic base is used to take up the hydrogen halide formed in the reaction, suitable bases being triethylamine (TEA) and Hünig's Base. Suitable reaction media include halogenated solvents, such as methylene chloride and chloroform. The reaction is preferably run at low temperature, at least initially. Suitable temperatures are in the region of –50° C. down to –80° C. Later in the reaction it may be desirable to allow the mixture to warm up to about RT to ensure completion of the reaction.

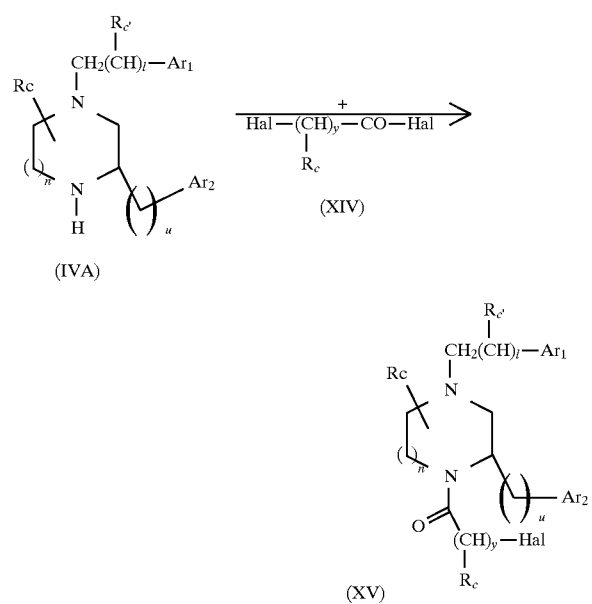

Reaction of the halogenated amides of formula XV with an amine of formula Z-H results in formation of the products of formula XVI, which are compounds of the invention in which X is O and m is 1. Compounds of formula XVI have been modified to show the fact that these products could have been prepared from compounds of formula IVA as well as from IV. Suitable solvents for this reaction are halogenated hydrocarbons, such as methylene chloride, and an organic base is present to absorb the H-Hal formed. Appropriate bases include Hünig's Base. The reaction is performed at or around RT, a suitable temperature being generally in the range of from 0° C. to 40° C. Reaction is complete within 1 to 48 hours.

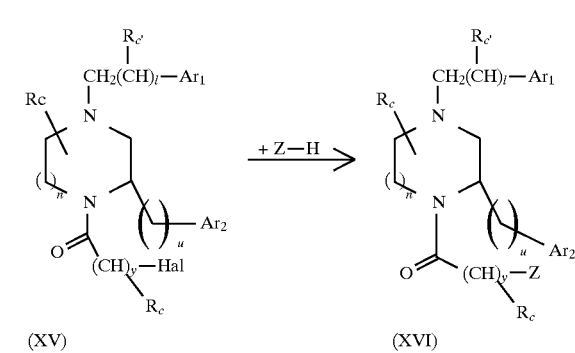

Method 5. Compounds of formula XVI where $y \neq 0$ may be converted to other compounds of the invention of formula XVII by reduction under controlled conditions.

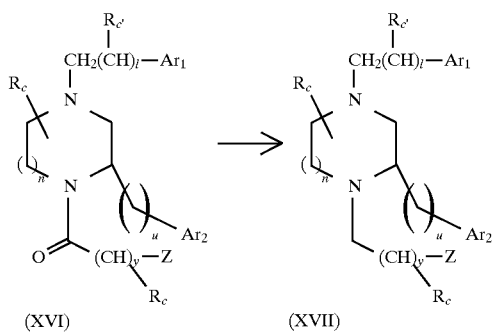

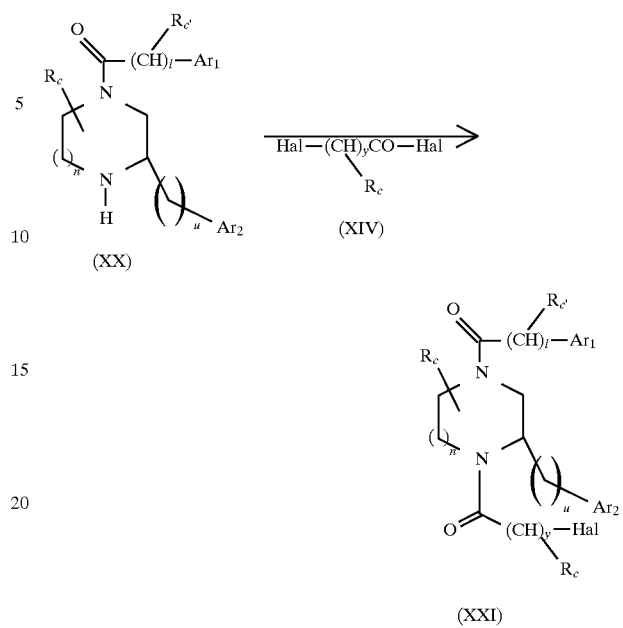

Suitable reducing agents to effect this transformation include the borane-dimethyl sulfide complex, as well as other less selective reagents, such as LAH, (assuming that no other group reactive to LAH is present), Red-Al®, and diborane in ether. Effective temperatures for the borane-dimethylsulfide complex to reduce compounds of formula XVI, range from RT to the reflux temperature of the solution of the reagent in THF (about 80° C.).

Method 6. Intermediates of the formula XVIII may be selectively acylated by coupling with an acid of the formula XIX. Standard coupling techniques may be applied, an example being the use of HOBT, a water-soluble carbodimide, such as DEC, and an organic base, such as triethylamine, in a non-hydroxylic solvent, such as $CH_2Cl_2$, at a temperature of about −20° C. initially. The mixture may be allowed to warm to RT to complete the reaction. The product of reaction is the amide of formula XX.

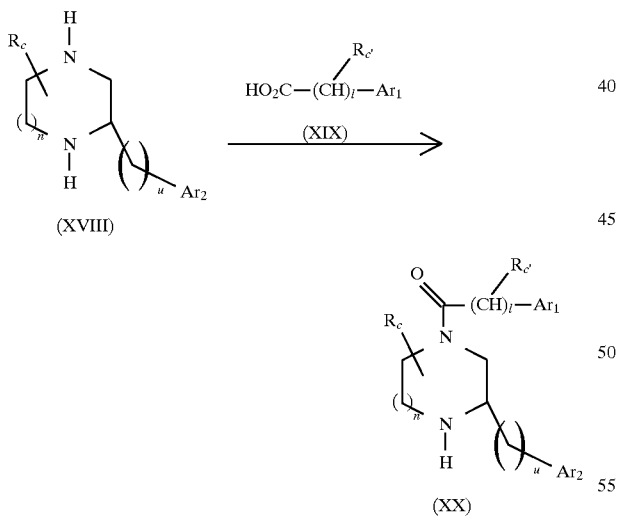

Compounds of the formula XX, may be further acylated using an acid halide of formula XIV. The reaction is run, preferably at about −78° C., over a period of 1 to 12 hours, in a halogenated solvent, such as methylene chloride or similar solvent. An organic tertiary amine is used to absorb the H-Hal produced in the reaction. Suitable amines include triethylamine and Hünig's Base. As used herein Hal means Cl, Br, or I.

The compounds of formula XXI, that is, m is 1 in formula I, y=1–3, l=0–2 may be used for further reaction without isolation. Additional organic base, for instance, Hünig's Base, is added to the mixture followed by Z-H, at or around −78° C. The reaction is completed by allowing the mixture to warm to RT overnight yielding the compounds of formula XXII after work-up and purification by standard methods.

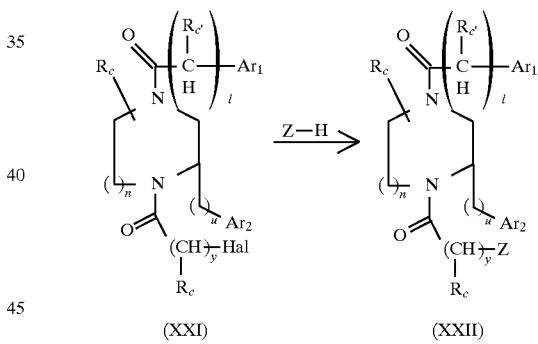

The compounds of formula XXII, in which y=1–3 may be converted to other products of formula XXIII by reduction under controlled conditions.

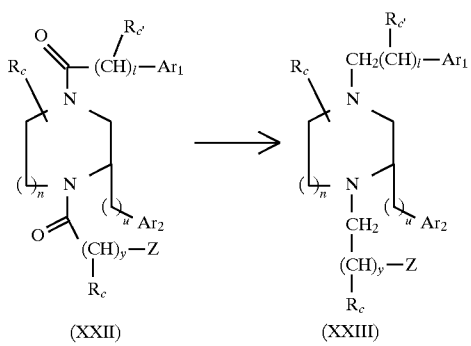

Suitable reducing agents to effect this transformation include the borane-methyl sulfide complex, as well as other less selective reagents, such as LAH, Red-Al®), and diborane in ether or other unreactive solvents, such as THF. Using the borane-methyl sulfide complex in THF, at the reflux temperature of the solution, which is about 80° C., the reaction is complete in about 2 hours to 48 hours depending on the precise substrate.

Some of the substrates Z-H for the alkylation reaction were synthesized from diamino compound (A) by initial conversion to the t-BOC protected derivative(B) followed by removal of the benzyl group by hydrogenolysis over a suitable catalyst such as $Pd(OH)_2$ to yield the t-BOC protected derivative (C). Subsequent elaboration of (C) can be accomplished by either alkylation or reductive alkylation depending on the availability of reagents for these reactions.

Reaction of the intermediate (C) with an aldehyde or ketone (D) under the conditions of reductive amination, such as in methanol and in the presence of $NaBH_3CN$ with sufficient AcOH (acetic acid) present to allow the reaction to proceed at a suitable rate, produces the amine (E) from which the t-BOC group may be removed with 4N-HCl in dioxane followed by basification, for instance, with an aqueous solution of NaOH, to produce the compound of formula (F).

The same product, (Ea), may be prepared from (C) by alkylation with the halide derivative (G) in which "Hal" is Cl, Br, or I. Other activated leaving groups are also possible for this reagent, such as mesylates or tosylates. The reagent is preferably primary but the reaction can also often be made to work acceptably for secondary derivatives.

The product of the alkylation, (Ea), may be treated as described above to produce the reagent (Fa) which represents one of the preferred forms of Z which can be used to convert a compound of formula XXI to a compound of formula XXII.

The intermediate (C) (below) may also be modified by acylation, for instance with an acid halide of formula (H), to produce the intermediate (I), in which $n_3 \neq 0$. Removal of the BOC protecting group, as described previously, leads to the amine (J) which represents one of the preferred forms of Z. This may be used to convert a compound of formula (XXI) to a compound of the invention, as described above.

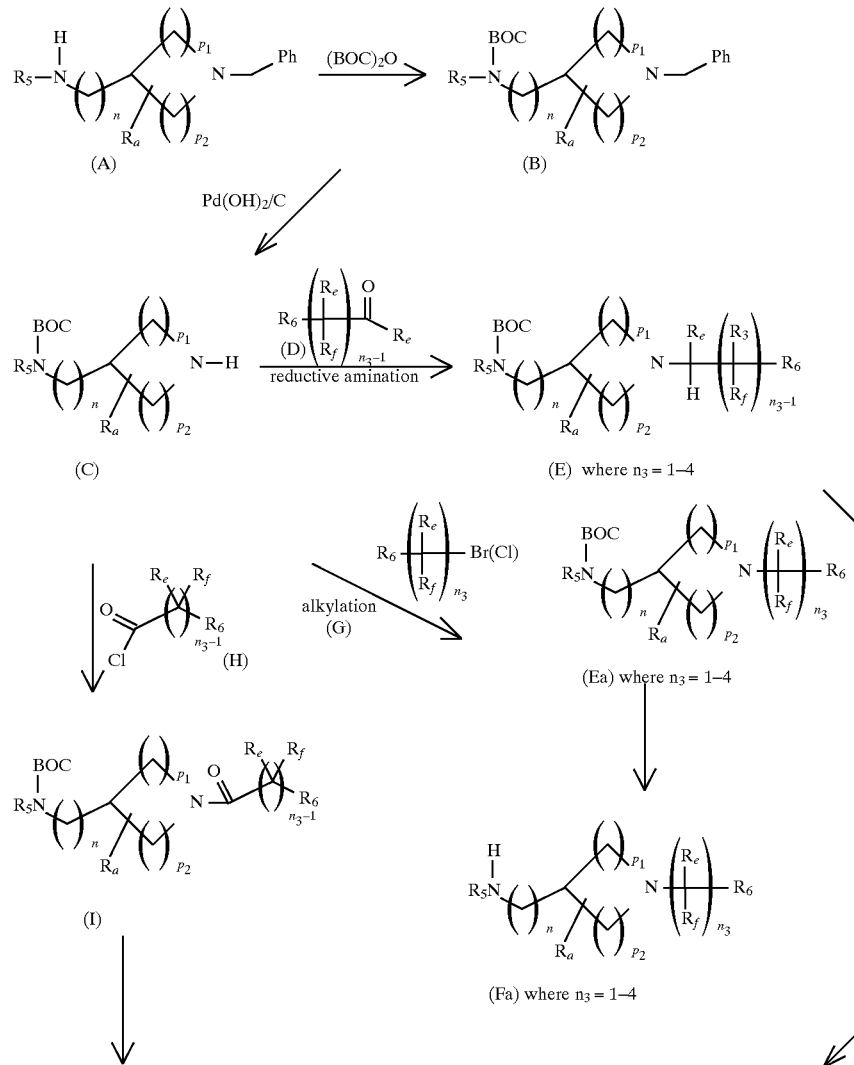

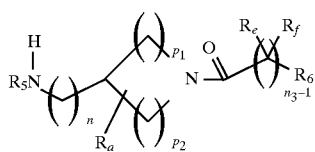

(J)

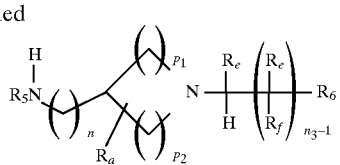

(F) where $n_3 = 1$–$4$

Method 6a A useful intermediate for certain variations in the group Z is the compound (K). This may be prepared from (XXI) and the protected amine (L). The starting material for this process is the N-BOC protected amine (M) which may be converted to (L) by standard techniques involving formation of the oxime using hydroxylamine hydrochloride in pyridine followed by reduction with hydrogen over Raney nickel in ethanol solution. Removal of the protecting group from (K), under conditions described previously, results in the amine (N).

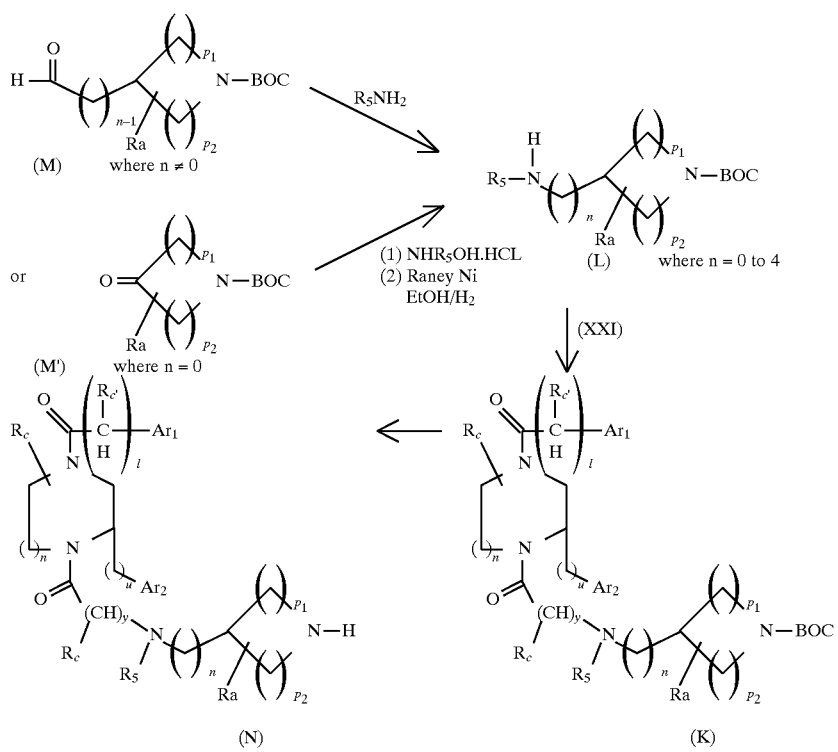

Use of this intermediate under conditions of acylation, under controlled conditions, results in reaction at the ring nitrogen atom to yield products such as (O). Either the acid halide, e.g. chloride (P), may be used, or a coupling reaction with a carboxylic acid may be used under conditions essentially similar to those described earlier using a water-soluble carbodimide reagent, for instance.

Sometimes the starting material (N) is provided as a salt, such as the HCl salt. In this case, it is necessary to add an organic tertiary base, such as Hünig's base to produce the free amine.

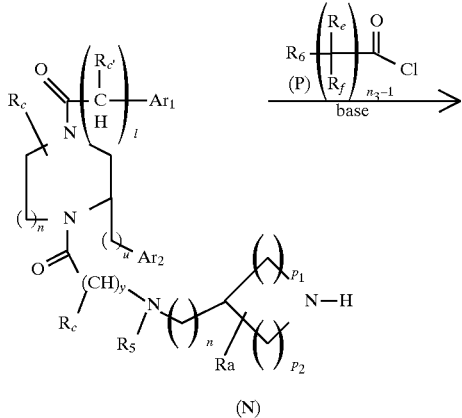

(N)

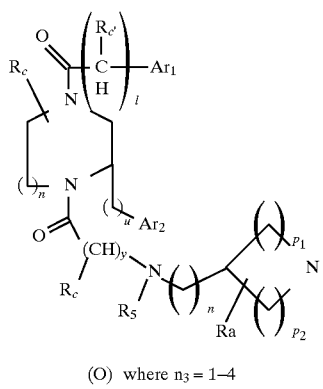

(O) where $n_3 = 1-4$

Alkylation of (N) may be accomplished with a suitable halogen-containing reagent, for instance, to produce (Q). Reagents such as (G) may be used for this conversion.

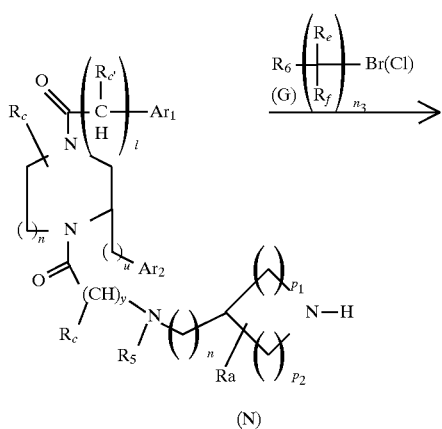

(N)

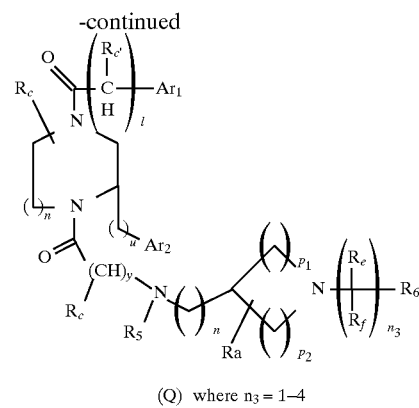

(Q) where $n_3 = 1-4$

In some cases, one of the —C($R_e$)($R_f$)— groups may be a carbonyl group with the exception that the carbon in the carbonyl can not be directly attached to the nitrogen atom since these products are amides which are described above.

Under certain circumstances, specifically where at least one of the groups $R_e$ and $R_f$ on the carbon atom to be directly attached to the ring nitrogen is H, then a reductive alkylation reaction may be performed, as described previously, to produce the compound of the invention (R). The reagent used for this conversion is (D), an aldehyde (if Re=H) or ketone.

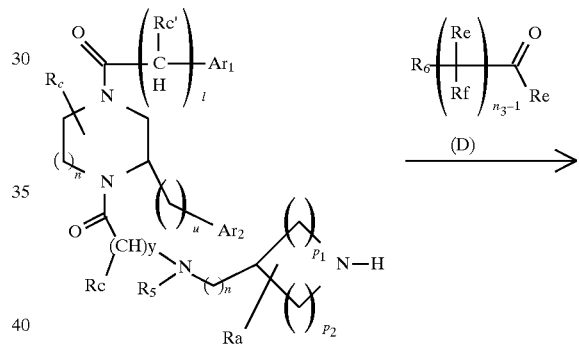

(N)

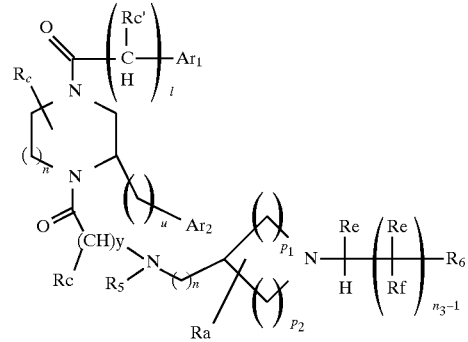

(R)

where $n_3 = 1-4$

Method 7. The acylated derivatives of formula XX from Method 6 may be reduced to the saturated alkyl chain derivatives of formula IVA.

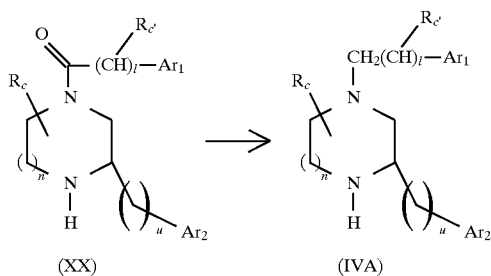

The process to conduct this conversion is the same as described in Method 6 for conversion of a compound of formula XXII to a compound of formula XXIII. The reagent of preference is the borane-methyl sulfide complex.

A compound of formula IVA can be converted to a target compound of formula XVI as described previously.

An alternate route to compounds of structure (XXII) also starts with compound (XVIII). Initial reaction with an amine protecting group reagent, preferably BOC anhydride, produces the N-t-butyloxycarbonyl derivative of the formula XXVIII.

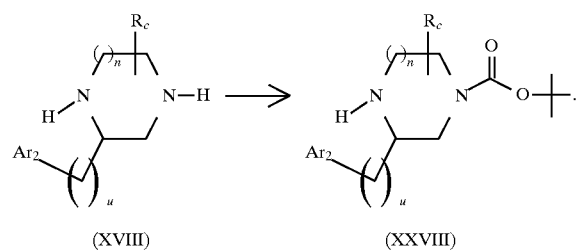

As before, reaction occurs preferentially at the nitrogen atom further away from the $Ar_2$ group. Reaction of this intermediate with a reagent of structure (XIV) as described above, leads to the halo-derivative (XXIX). Reaction of (XXIX) with Z-H, again as described above, produces the intermediate (XXX) which may be de-protected to produce (XXXI). Suitable reagents include trifluoroacetic acid and HCl.

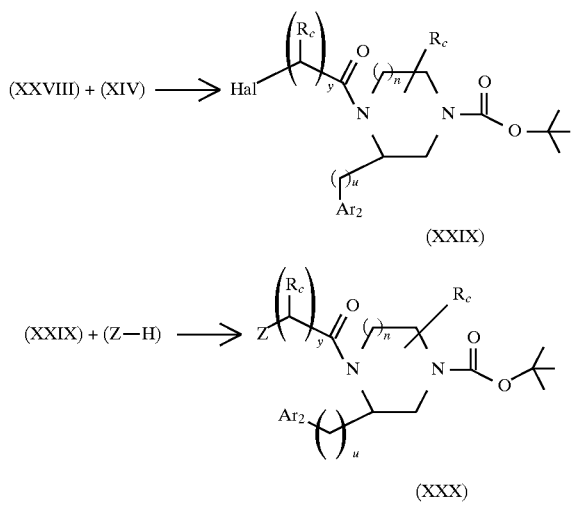

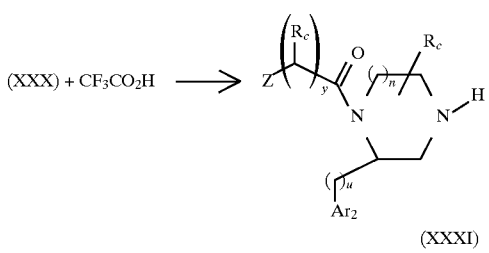

Reaction of (XXXI) with a carboxylic acid (XIX) under such coupling conditions as described above, leads to the products of formula (XXII).

Method 7a. Synthesis of the compounds of the invention wherein the pendant aromatic group $Ar_2$, or the pendant aromatic group $Ar_2$ and its sidechain, are located in the alternate ring position to the compounds of formula XXII (i.e. compounds of formula C below), may be prepared using compounds of formula XXVIII from method 7 as starting materials. Coupling of compounds of formula XXVIII with any of the acids

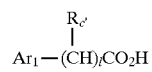

under standard coupling conditions, for instance using HOBT, $Et_3N$ and DEC in $CH_2Cl_2$, produces the intermediate (A). Removal of the t-BOC or other protecting group under standard conditions releases the free amine (B). Acylation of (B) and further reaction with Z-H proceeds as described in Method 6 for the conversion of (XX) via (XXI) to (XXII) to produce compound (C) of the invention.

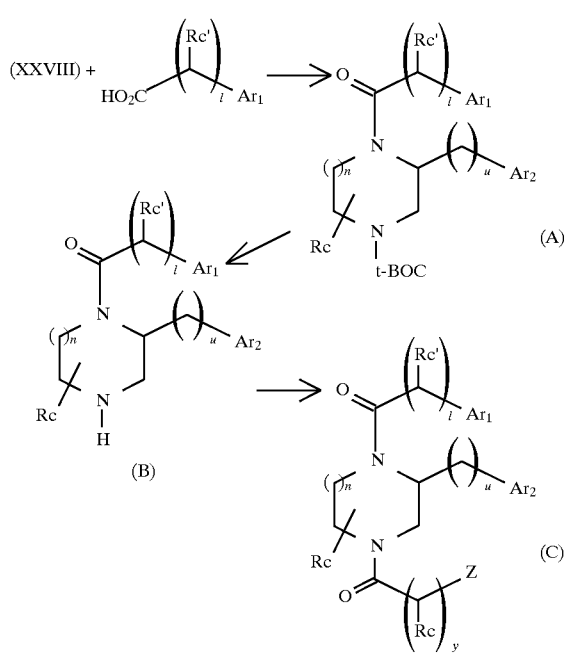

Method 8. A method for introducing a group, $R_c$, into the sidechain of a compound of the invention begins with a previously prepared compound of formula (XX). This may be coupled with a suitably protected amino-acid derivative of formula (XXXII) in which the t-BOC group is used as a representative protecting group. Use of a relatively reactive coupling agent, such as BOP-Cl of formula (XXXIII), is preferred and the reaction is run under standard coupling conditions well known to one skilled in the art. Suitable conditions include the use of $CH_2Cl_2$ and/or DMF as solvent, with triethylamine or Hünig's Base, and a temperature between 0° C. initially and RT. Usual work-up conditions yield the protected intermediate of formula (XXXIV).

In the case of (XXXIV), in which the N-protecting group is t-BOC, the usual conditions for removal of such a group may be used to free the amine function. Various concentrations of $CF_3CO_2H$ in $CH_2Cl_2$ will usually suffice. In some substrates a fairly dilute solution (e.g. 2N) will be sufficient whereas in other cases a more concentrated solution, up to neat TFA, may be necessary. In addition, other N-protecting groups may be employed and removed by methods well known in the art. An example is use of the N-Cbz which may be removed under either acidic or hydrogenolytic conditions. The result of deprotection is the amine intermediate of the formula (XXXV).

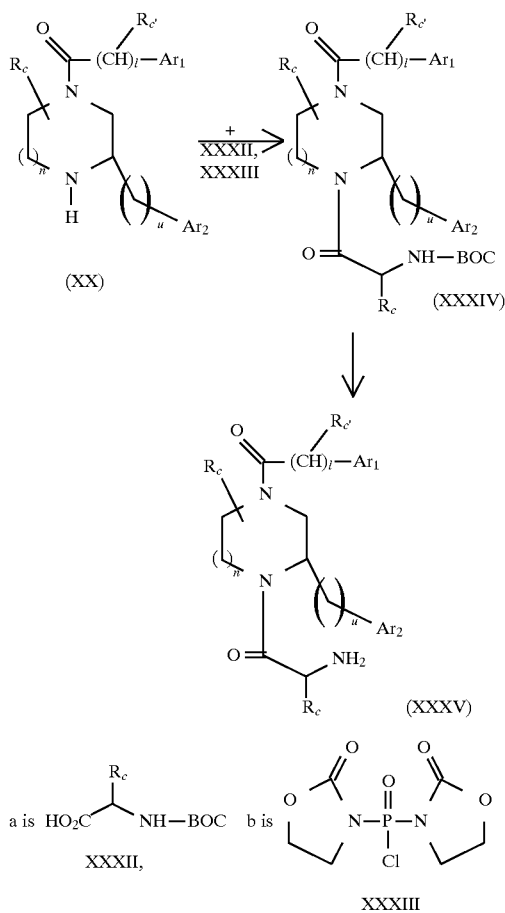

Conversion of intermediate of the formula (XXXV) to compounds of the invention is then carried out by a reductive alkylation process.

The group Z is introduced into the molecule using an aldehyde or ketone in which the aforementioned group is present at the carbon atom that is to be joined to the amino group of the formula (XXXV). An example of such an intermediate is a compound of the formula (XXXVI).

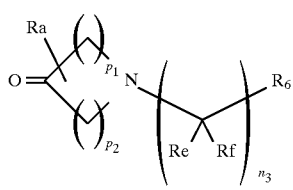

After the reaction this group becomes the Z group of the compounds of the invention, that is, the "Y-NH" group shown in compounds of the formula (XXXVII) just below

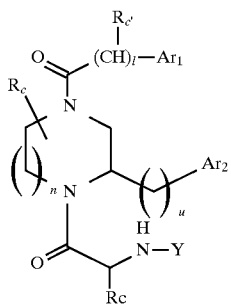

is equivalent to the "Z" group shown in the Summary of the Invention. Conditions for this reductive amination procedure are known in the art and are exemplified by the use of $NaBH_3CN$ in MeOH with the addition of several equivalents of acetic acid. Generally, the reaction is performed at RT and is left to react overnight.

Product is isolated by standard means, such as decomposition of excess reagent with $H_2O$ and extraction of the product into an organic solvent such as $CH_2Cl_2$ or a mixture of $Et_2O$ and $CH_2Cl_2$.

Using procedures similar to those described in the above or using procedures known to those skilled in the art, one can produce all of the compounds of formula I of the invention. For example, one can obtain compounds of the invention of formula I wherein the $R_c$ moiety is on various carbons of the piperazine ring.

The in vitro and in vivo activity of the compounds of formula I can be determined by the following procedures.

In Vitro Procedure to Identify $NK_1$ Activity

Test compounds are evaluated for their ability to inhibit the activity of the $NK_1$ agonist Substance P on the isolated guinea pig vas deferens. Freshly cut vas deferens are removed from male Hartley guinea pigs (230–350 g) and suspended in 25 ml tissue baths containing Kreb's Henseleit solution warmed to 37° C. and constantly aerated with 95% $O_2$ and 5% $CO_2$. Tissues are adjusted to 0.5 g and allowed to equilibrate for a period of 30 minutes. The vas deferens are exposed to an electrical field stimulation (Grass S48 Stimulator) every 60 seconds at an intensity that will cause the tissue to contract 80% of its maximum capacity. All responses are recorded isometrically by means of a Grass force displacement transducer (FT03) and Harvard electronic recorder. Substance P inhibits the electrical field stimulated-induced contractions of the guinea pig vas deferens. In unpaired studies, all tissues (control or drug treated) are exposed to cumulative concentrations of Substance P ($1 \times 10^{-10}$M–$7 \times 10^{-7}$M). Single log-concentrations of the test compounds are given to separate tissues and allowed to equilibrate for 30 minutes before a Substance P concentration-response curve is generated. At least 5 separate tissues are used for each control and individual drug-concentration for every drug assay.

Inhibition of the Substance P is demonstrated by a rightward shift of its concentration-response curve. These shifts are used to determine the $pA_2$ value, which is defined as the negative log of the molar concentration of the inhibitor which would require that twice as much agonist be used to elicit a chosen response. This value is used to determine relative antagonist potency.

Isolated Hamster Trachea $NK_2$ Assay

General methodology and characterization of hamster trachea responses to neurokinin agonists as providing an $NK_2$ monoreceptor assay is found in C. A. Maggi, et al., *Eur. J. Pharmacol.* 166 (1989) 435 and J. L. Ellis, et al., *J. Pharm. Exp. Ther.* 267 (1993) 95.

Continuous isometric tension monitoring is achieved with Grass FT-03 force displacement transducers connected to Buxco Electronics preamplifiers built into a Graphtec Linearcorder Model WR 3310.

Male Charles River LAK:LVG (SYR) hamsters, 100–200 g fed weight, are stunned by a sharp blow to the head, loss of corneal reflex is assured, the hamsters are sacrificed by thoracotomy and cutting the heart. Cervical trachea segments are removed to room temperature Krebs buffer, pH 7.4, aerated with 95% $O_2$–5% $CO_2$ gas and cleaned of adhering tissue. The segments are cut into two 3–4 mm long ring segments. Tracheal rings are suspended from transducers and anchored in 15.0 ml water jacketed organ baths by means of stainless steel hooks and 6-0 silk. Baths are filled with Krebs buffer, pH 7.4, maintained at 37° C. and continuously aerated with 95% $O_2$–5% $CO_2$ gas. Tracheal rings are placed under 1.0 g initial tension and allowed a 90 min equilibration period with four 1 $\mu$M NKA challenge, wash and recovery cycles at 20 min intervals. 30 min vehicle pretreatment is followed by cumulative additions of rising doses of NKA (3 nM–1 $\mu$M final concentration, 5 min intervals between additions). The final NKA response is followed by a 15 min wash and recovery period. 30 min pretreatment with a test compound or its vehicle is followed by cumulative additions of rising doses of NKA (3 nM–10 $\mu$M final concentration if necessary, 5 minutes intervals between additions). The final NKA response is followed by a 1 mM carbachol challenge to obtain a maximal tension response in each tissue.

Tissue responses to NKA are recorded as positive pen displacements over baseline and converted to grams tension by comparison to standard weights. Responses are normalized as a % of the maximal tissue tension. $ED_{50}$'s are calculated for NKA from the control and treated NKA dose responses and compared. Test compounds resulting in an agonist dose ratio$\geq 2$ at a screening concentration of 1 $\mu$M (i.e. $pA_2 \geq =6.0$) are considered actives. Further dose response data is obtained for actives so that an apparent $pA_2$ estimate can be calculated. $pA_2$ is calculated either by estimation of $K_i$ as described by Furchgott (where $pA_2 = -\text{Log } K_i$, R. F. Furchgott, *Pharm. Rev.* 7 [1995] 183) or by Shild Plot Analysis (O. Arunlakshana & H. O. Shild, *Br. J. Pharmacol.* 14[1959] 48) if the data is sufficient.

Effect of $NK_1$ Antagonists on Substance P-Induced Airway Microvascular Leakage in Guinea Pigs Studies are performed on male Hartley guinea pigs ranging in weight from 400–650 g. The animals are given food and water ad libitum. The animals are anesthetized by intraperitoneal injection of dialurethane (containing 0.1 g/ml diallylbarbituric acid, 0.4 g/ml ethylurea and 0.4 g/ml urethane). The trachea is cannulated just below the larynx and the animals are ventilated ($V_T$=4 ml, f=45 breaths/min) with a Harvard rodent respirator. The jugular vein is cannulated for the injection of drugs.

The Evans blue dye technique (Danko, G. et al., *Pharmacol. Commun.*, 1, 203–209, 1992) is used to measure airway microvascular leakage (AML). Evans blue (30 mg/kg) is injected intravenously, followed 1 min later by i.v. injection of substance P (10 $\mu$g/kg). Five min later, the thorax is opended and a blunt-ended 13-guage needle passed into the aorta. An incision is made in the right atrium and blood is expelled by flushing 100 ml of saline through the aortic catheter. The lungs and trachea are removed en-bloc and the trachea and bronchi are then blotted dry with filter paper and weighed. Evans blue is extracted by incubation of the tissue at 37° C. for 18 hr in 2 ml of formamide in stoppered tubes. The absorbance of the formamide extracts of dye is measured at 620 nm. The amount of dye is calculated by interpolation from a standard curve of Evans blue in the range 0.5–10 $\mu$g/ml in formamide. The dye concentration is expressed as ng dye per mg tissue wet weight. Test compounds were suspended in cyclodextran vehicle and given i.v. 5 min before substance P.

Measurement of $NK_2$ Activity In Vivo

Male Hartley guinea pigs (400–500 gm) with ad lib. access to food and water are anesthetized with an intraperitoneal injection of 0.9 ml/kg dialurethane (containing 0.1 g/m diallylbarbituric acid, 0.4 g/ml ethylurea and 0.4 g/ml urethane). After induction of a surgical plane of anesthesia, tracheal, esophageal and jugular venous cannulae are implanted to facilitate mechanical respiration, measurement of esophageal pressure and administration of drugs, respectively.

The guinea pigs are placed inside a whole body plethysmograph and the catheters connected to outlet ports in the plethysmograph wall. Airflow is measured using a differential pressure transducer (Validyne, Northridge Calif., model MP45-1, range±2 cm $H_2O$) which measures the pressure across a wire mesh screen that covers a 1 inch hole in the wall of the plethysmograph. The airflow signal is electrically integrated to a signal proportional to volume. Transpulmonary pressure is measured as the pressure difference between the trachea and the esophagus using a differential pressure transducer (Validyne, Northridge, Calif., model MP45-1, range±20 cm $H_2O$). The volume, airflow and transpulmonary pressure signals are monitored by means of a pulmonary analysis computer (Buxco Electronics, Sharon, Conn., model 6) and used for the derivation of pulmonary resistance ($R_L$) and dynamic lung compliance ($C_{Dyn}$).

Bronchoconstriction Due to NKA

Increasing iv doses of NKA are administered at half log (0.01–3 $\mu$g/kg) intervals allowing recovery to baseline pulmonary mechanics between each dose. Peak bronchoconstriction occurs within 30 seconds after each dose of agonist. The dose response is stopped when $C_{Dyn}$ is reduced 80–90% from baseline. One dose-response to NKA is performed in each animal. Test compounds are suspended in cyclodextran vehicle and given i.v. 5 min before the initiation of the NKA dose response.

For each animal, dose response curves to NKA are constructed by plotting the percent increase in $R_L$ or decrease in $C_{Dyn}$ against log dose of agonist. The doses of NKA that increased $R_L$ by 100% ($R_L 100$) or decreased $C_{Dyn}$ by 40% ($C_{Dyn} 40$) from baseline values are obtained by log-linear interpolation of the dose response curves.

Neurokinin Receptor Binding Assay(s)

Chinese Hamster ovary (CHO) cells transfected with the coding regions for the human neurokinin 1 ($NK_1$) of the human neurokinin 2 ($NK_2$) receptors are grown in Dulbecco's minimal essential medium supplemented with 10% fetal calf serum, 0.1 mM non-essential amino acids, 2 mM glutamine, 100 units/ml of penicillin and streptomycin, and 0.8 mg of G418/ml at 37° C. in a humidified atmosphere containing 5% $CO_2$.

Cells are detached from T-175 flasks with a sterile solution containing 5 mM EDTA in phosphate buffered saline. Cells are harvested by centrifugation and washed in RPMI media at 40° C. for 5 minutes. The pellet is resuspended in Tris-HCl (pH 7.4) containing 1 $\mu$M phosphoramidon and 4 ug/ml of chymostatin at a cell density of $30 \times 10^6$ cells/ml. The suspension is then homogenized in a Brinkman Polytron (setting 5) for 30–45 seconds. The homogenate is centrifuged at 800×g for 5 min at 4° C. to collect unbroken cells and nuclei. The supernatant is centrifuged in a Sorvall RC5C at 19,000 rpm (44,00×g) for 30 min at 4° C. The pellet is resuspended, an aliquot is removed for a protein determination (BCA) and washed again. The resulting pellet is stored at –80° C.

To assay receptor binding, 50 $\mu$l of [$^3$H]-Substance P (9-Sar, 11-Met [02]) (specific activity 41 Ci/mmol) (Dupont-NEN) (0.8 nM for the NK-1 assay) or [$^3$H]-Neurokinin A (specific activity 114 Ci/mmole) (Zenca) (1.0 nM for the NK-2 assay) is added to tubes containing buffer (50 mM Tris-HCl (pH 7.4) with 1 mM MnCl$_2$ and 0.2% Bovine Serum Albumin) and either DMSO or test compound. Binding is initiated by the addition of 100 $\mu$l of membrane (10–20 $\mu$g) containing the human NK-1 or NK-2 receptor in a final volume of 200 $\mu$l. After 40 minutes at room temperature, the reaction is stopped by rapid filtration onto Whatman GF/C filters which have been presoaked in 0.3% polyethylenimine. Filters are washed 2 times with 3 ml of 50 mM Tris-HCl (pH7.4). Filters are added to 6 mls of Ready-Safe liquid scintillation cocktail and quantified by liquid scintillation spectrometry in a LKB 1219 RackBeta counter. Non-specific binding is determined by the addition of either 1 $\mu$M of CP-99994 (NK$_1$) or 1 $\mu$M SR-48968 (NK$_2$) (both synthesized by the chemistry department of Schering-Plough Research Institute). IC$_{50}$ values are determined from competition binding curves and Ki values are determined according to Cheng and Prusoff using the experimentally determined value of 0.8 nM for the NK$_1$ receptor and 2.4 nM for the NK$_2$ receptor.

For all of the compounds of the invention, the NK$_1$ binding is in a range of about 0–100% inhibition at 1 $\mu$M concentration. For all of the compounds of the invention, the NK$_2$ binding is in a range of about 0–100% inhibition at 1 $\mu$M concentration. It should be understood that while the NK binding for certain compounds of the invention is as low as 0% at 1 $\mu$M concentration, that at higher concentrations these compounds are expected to have NK binding inhibition activity.

The K$_i$ of a compound is that concentration at which the compound caused 50% inhibition of either NK$_1$ or NK$_2$. For those compounds of the invention having higher than 50% inhibition of NK$_1$, K$_i$'s for NK$_1$ were determined. The K$_i$'s for NK$_1$ for such compounds fell within a range of about 0.1 nM to about 1 $\mu$M.

For those compounds of the invention having higher than 50% inhibition of NK$_2$, K$_i$'s for NK$_2$ were determined. The K$_i$'s for NK$_2$ for such compounds fell within a range of about 0.1 nM to about 1 $\mu$M.

Compounds of formula I exhibit NK$_1$ and NK$_2$ antagonist activity to varying degrees, i.e., certain compounds have strong NK$_1$ antagonist activity, but weaker NK$_2$ antagonist activity. Others are strong NK$_2$ antagonists, but weaker NK$_1$ antagonists. Certain compounds have both strong NK$_1$ and NK$_2$ antagonist activities. Some compounds can also be NK$_3$ antagonists.

NK$_1$ binding and NK$_2$ binding values for certain compounds of the invention are as follows:

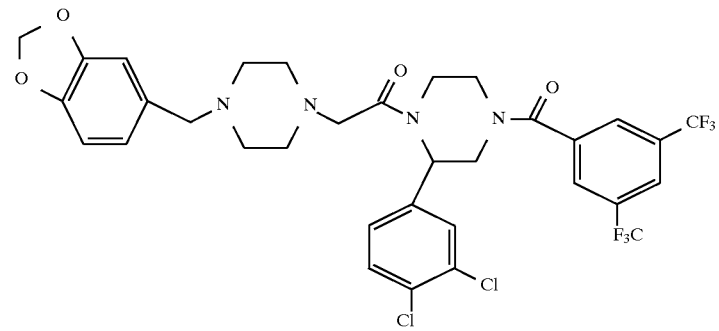

has a K$_i$ for NK$_1$ binding, of 5.3 nM; and has a K$_i$ for NK$_2$ binding of 511 nM.

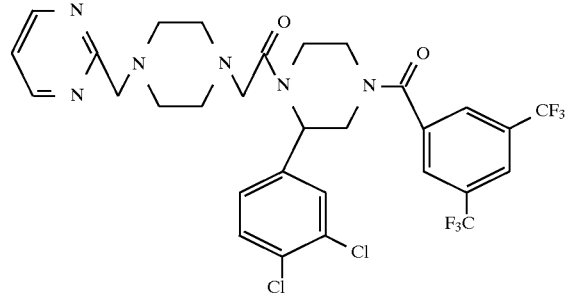

has a K$_i$ for NK$_1$ binding, of 23.3 nM; and a K$_i$ for NK$_2$ binding, of 29.1 nM.

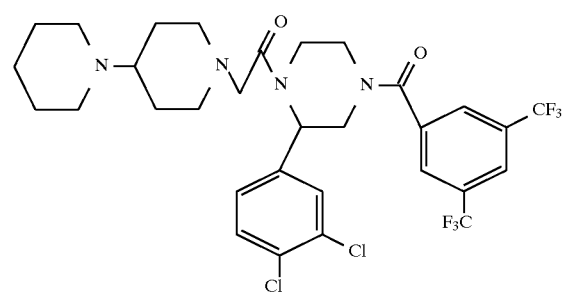

has a K$_i$ for NK$_1$ binding, of 3.3 nM; and a K$_i$ for NK$_2$ binding, of 93 nM.

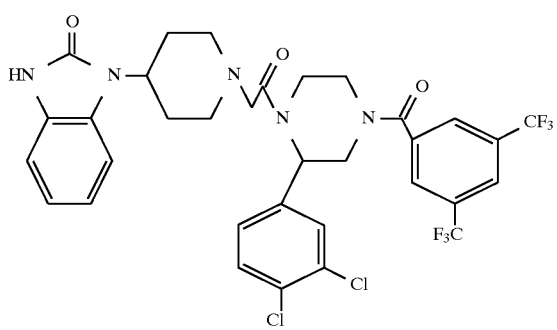

has a $K_i$ for $NK_1$ binding, of 9.6 nM; and a $K_i$ for $NK_2$ binding, of 87 nM.

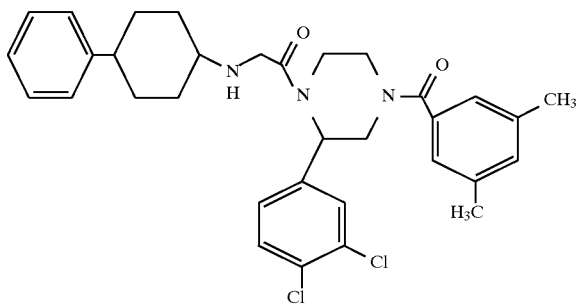

has a $K_i$ for $NK_1$ binding, of 7.0 nM; and a $K_i$ for $NK_2$ binding, of 40 nM.

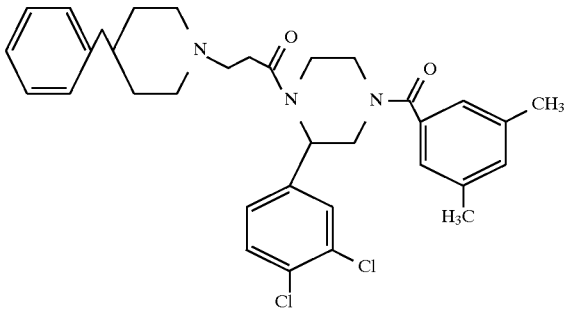

has a $K_i$ for $NK_1$ binding, of 71 nM; and a $K_i$ for $NK_2$ binding, of 7.5 nM.

(Enantiomer B)

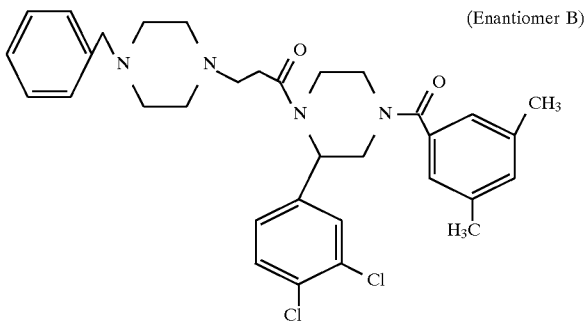

has a $K_i$ for $NK_1$ binding, of 67 nM; and a $K_i$ for $NK_2$ binding, of 18 nM.

(Racemic compound)

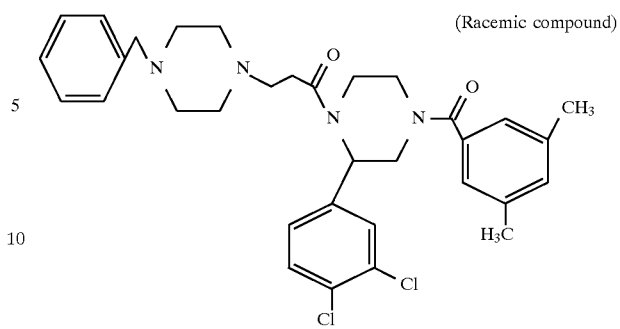

has a $K_i$ for $Nk_1$ binding, of 3 nM; and a $K_i$ for $Nk_2$ binding, of 25 nM.

Many compounds of formula I have an asymmetric center and therefore exist as a pair of enantiomers. In such cases, one enantiomer can have different biological activity than the other. For example, one enantiomer can have strong $NK_1$ activity and weak $NK_2$ activity while the other enantiomer has weak $NK_1$ activity and strong $NK_2$ activity.

Certain compounds of formula I have been found to be antagonists of both $NK_1$ and $NK_2$ receptors, and are therefore useful in treating conditions caused or aggravated by the activity of $NK_1$ and $NK_2$ receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution. The pharmaceutical compositions can be prepared with conventional excipients and additives, using well known formulation techniques. Pharmaceutically acceptable excipients and additives include nontoxic and chemically compatible fillers, binders, disintegrants, buffers, preservatives, antioxidants, lubricants, flavorings, thickeners, coloring agents, emulsifiers and the like.

The daily dose of a compound of formula I for treating asthma, cough, bronchospasm, inflammatory disease, migraine, nociception and gastrointestinal disorders is about 0.1 mg to about 20 mg/kg of body weight per day, preferably about 0.5 to about 15 mg/kg, more preferably 0.5 to about 5 mg/kg. For an average body weight of 70 kg, the dosage range is therefore from about 1 to about 1500 mg of drug per day, preferably about 50 to about 100 mg, given in a single dose or 2–4 divided doses. The exact dose, however is determined by the attending clinician, and is dependent on the potency of the compound administered, the age, weight, condition and response of the patient.

The invention disclosed herein is exemplified by the following examples, which should not be construed to limit the scope of the disclosure. Alternative mechanistic pathways and analogous structures within the scope of the invention will be apparent to those skilled in the art.

EXAMPLE 1

Preparation of (+/−)-1-[[3,5-bis(trifluoromethyl)phenyl]methyl]-3-phenyl-piperazine, dihydrochloride salt.

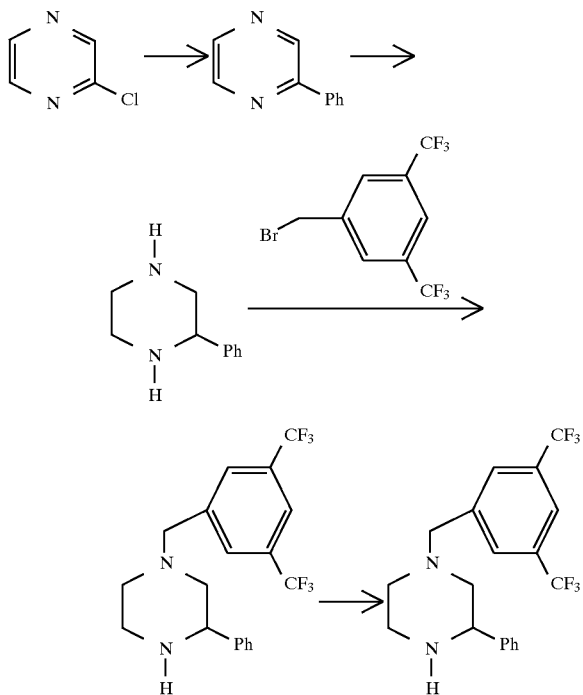

Chloropyrazine (20.68 g, 177 mmol) and [1,2-bis(diphenylphosphino)ethane]nickel(II) chloride (41.08 g, 77.8 mmol) in dry THF (1.5 L) were mixed and stirred for 80 minutes in a flask (cooled with a water bath) under nitrogen. A solution of phenylmagnesium bromide (3M in Et$_2$O) (103 mL, 309 mmol) was added slowly through a dropping funnel into the cooled brick-red slurry at room temperature under nitrogen over 3.5 hours. After stirring at room temperature overnight, TLC showed that the reaction was complete. 3N HCl (100 mL) was added slowly through a dropping funnel under nitrogen and the mixture was stirred for one hour. The THF layer was separated from the aqueous layer. The aqueous layer was adjusted to pH 12 with 6N NaOH and extracted with EtOAc (100 mL, 3×). The organic fractions (THF and EtOAc) were combined and dried over MgSO$_4$, filtered and concentrated to give a solid. The product was purified by flash chromatography on 300 g of flash grade silica gel in 2.5% EtOAc/CH$_2$Cl$_2$ to give 10.79 gram (69 mmol, 39%) of 2-phenylpyrazine, m.p. 69°–70° C.; FAB MS [M+1]$^+$ 157;

Found, C, 76.55; H, 5.22; N, 17.71. Calcd. for C$_{10}$H$_8$N$_2$, C, 76.90; H, 5.16; N, 19.93.

To a solution of 2-phenylpyrazine (11.64 g, 74.53 mmol) in acetic acid (58.2 mL) was added palladium acetate Pd(OAc)$_2$ (2.33 g, 9.94 mmol). The mixture was hydrogenated at 50 psi for 4 h. After the reaction was complete, the catalyst was filtered off and rinsed with a small portion of acetic acid. The filtrate was concentrated under house vacuum to give a brown-black solid which was suspended in deionized water (300 mL) and adjusted to pH 13 with 20% NaOH solution. The product was extracted from aqueous solution with EtOAc (200 mL, 3×), dried over MgSO$_4$, filtered and evaporated to dryness to give 2-phenylpiperazine (7.2 g). An additional 1.6 g of 2-phenylpiperazine was obtained by evaporating the aqueous fraction to a solid and triturating the solid with CH$_2$Cl$_2$. Total yield of 2-phenyl-piperazine was 73%. The crude material was crystallized from EtOAc and hexane for characterization, m.p. 86°–88° C.; FAB MS [M+1]$^+$ 163;

Found, C, 74.04; H, 8.66; N, 17.15. Calcd. for C$_{10}$H$_{14}$N$_2$, C, 74.04; H, 8.69; N, 17.26.

To a solution of 2-phenylpiperazine (4.0 g, 24.65 mmol) in dry CH$_2$Cl$_2$ (200 mL) at −78° C. under nitrogen was added Et$_3$N (5.15 mL, 36.97 mmol) followed by the dropwise addition of a CH$_2$Cl$_2$ solution(46.60 mL) of bis(trifluoromethyl)benzyl bromide (4.66 mL, 24.65 mmol). The flask was kept at −78° C. then it was gradually warmed to room temperature overnight. After TLC showed that the reaction was complete, the material was washed with brine (150 mL, 2×), dried over MgSO$_4$, filtered, and evaporated under vacuum to yield a tan solid. The crude product was purified by flash silica get chromatography (150 g), eluting with 2.5% MeOH/CH$_2$Cl$_2$ to give (+,−) 1-[[3,5-bis(trifluoromethyl)phenyl]methyl]-3-phenylpiperazine (6.96 g, 17.92 mmol, 72.7%) as an oil. A portion of this oil (0.5 g, 1.287 mmol)) was converted to its hydrochloride salt by dissolving the oil in CH$_2$Cl$_2$ (20 mL) and treating with 2.3M HCl-EtOH (1.3 mL 2.99 mmol). After stirring at room temperature for 10 minutes, all solvents were removed under high vacuum and the residue was dried overnight, m.p. 229°–233° C.; FAB MS [M+1]$^+$ 389;

Found, C, 48.83; H, 4.28; N, 5.87; Cl, 14.77; F, 24.03. Calcd. for C$_{19}$H$_{18}$N$_2$F$_6$.2 HCl.0.25 H$_2$O, C, 48.99; H, 4.43; N, 6.01; Cl, 15.22; F, 24.47.

EXAMPLE 2

Preparation of (+,−)-4-[[3,5-bis(trifluoromethyl)phenyl]methyl]-1-[2-(4-hydroxy-4-phenyl-1-piperidinyl)acetyl]-2-phenylpiperazine, dihydrochoride salt.

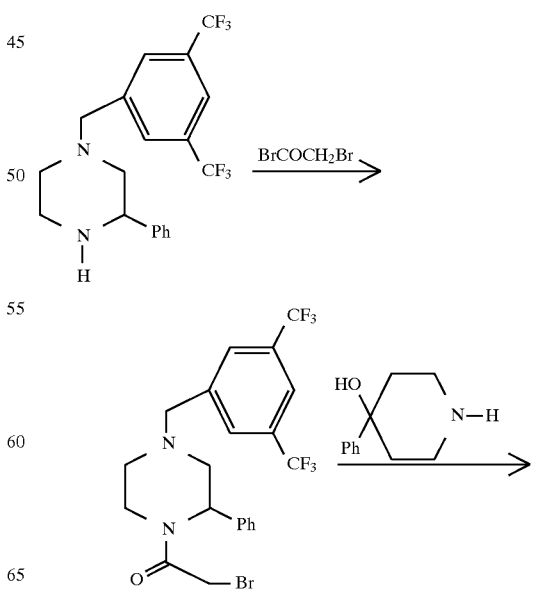

-continued

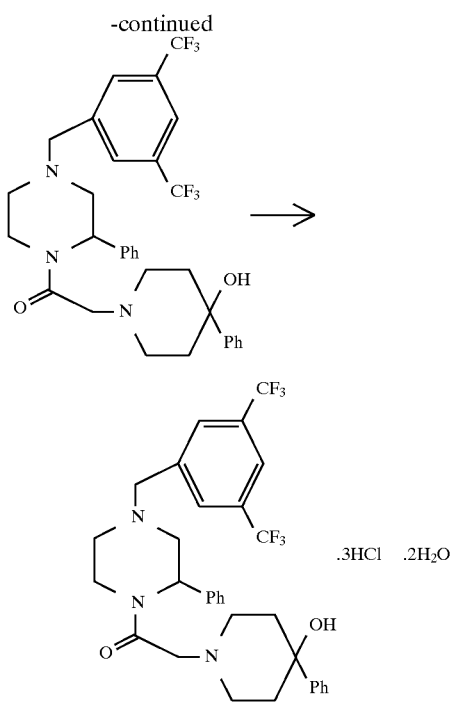

To a solution of (+,−) 1-[[3,5-bis(trifluoromethyl)phenyl]methyl]-3-phenylpiperazine (0.76 g, 1.975 mmol) in dry CH$_2$Cl$_2$ (15.2 mL) at −78° C. was added Et$_3$N (0.286 mL, 2.055 mmol) followed by the dropwise addition of bromoacetyl bromide (0.179 mL, 2.055 mmol). After stirring at −78° C. for 4 hours, the reaction was diluted with CH$_2$Cl$_2$ (200 mL), washed with brine (100 mL, 2×) and dried over MgSO$_4$. After filtration, the solvent was removed to give a light yellow solid which was used without further purification. FAB MS[M+1]$^+$ 509.2 ($^{79}$Br).

The product from the previous reaction (2.0 g, 3.928 mmol) was dissolved in dry CH$_2$Cl$_2$ (20 mL) and cooled to −78° C. under nitrogen. To this cooled solution were added 4-hydroxy-4-phenylpiperidine (0.8 g, 4.49 mmol) and diisopropylethylamine (0.787 mL, 4.492 mmol). The reaction was gradually warmed to room temperature overnight under nitrogen. After completion, CH$_2$Cl$_2$ (300 mL) was added and the organic layer was washed with brine (100 mL, 2×), dried over MgSO$_4$ and filtered. The filtrate was evaporated under vacuum to give a crude oil which was purified by flash chromatography on flash grade silica gel (100 g), eluting with 4.0% NH$_3$-MeOH-2.5% EtOH/CH$_2$Cl$_2$ to give a light yellow oil (2.24 g, 2.38 mmol, 94%). A portion of the oil (0.40 g, 0.661 mmol) was converted to its hydrochloride salt by dissolving in CH$_2$Cl$_2$ (8 mL) and treating with 2.3M HCl-EtOH (0.632 mL, 1.454 mmol). After stirring at room temperature for 30 minutes, solvent was evaporated and the residue was vacuum dried overnight, m.p. 185°–187° C.; FAB MS [M+1]$^+$ 606.6; Found, C, 54.58; H, 5.44; N, 5.75; Cl, 9.71; F, 16.11. Calcd. for C$_{32}$H$_{33}$O$_2$N$_3$F$_6$.2 HCl.1.5 H$_2$O, C, 54.47; H, 5.43; N, 5.96; Cl, 10.05; F, 16.16.

EXAMPLE 3

By process analogous to that described in Example 2, employing appropriate heterocyclic derivatives (Z group), as listed below, in place of 4-hydroxy-4-phenylpiperidine, the following compounds were prepared.

| Z | salt | m.p. °C. | [M + 1] FAB MS | High Res. MS |
|---|---|---|---|---|
| Ph, H$_3$CC—N(H)(O)— piperidine-N— | free form | 198–201 | 647.4 | |
| Ph-CH$_2$-piperazine-N— | 3 HCl.2 H$_2$O | 192–195 | 605.5 | |
| Ph-CH$_2$-piperidine-N— | 2 HCl.1.5 H$_2$O | 162–165 | 604.5 | |

| Z | salt | m.p. °C. | [M + 1] FAB MS | High Res. MS |
|---|---|---|---|---|
| (2,6-dimethylphenyl-piperazinyl-methyl) | free form | 66–68 | 619.3 | Cal'd 619.2872<br>Found 619.2856 |
| (MeO, PhS(O)CH2-piperidinyl) | free form | 68–71 | 682.3 | |

EXAMPLE 4

Preparation of (+,−)-1-[2-[4-[[3,5-bis(trifluoromethyl)phenyl]methyl]-2-phenyl-1-piperazinyl]ethyl]-4-phenyl-4-piperidinol, trihydrochloride salt.

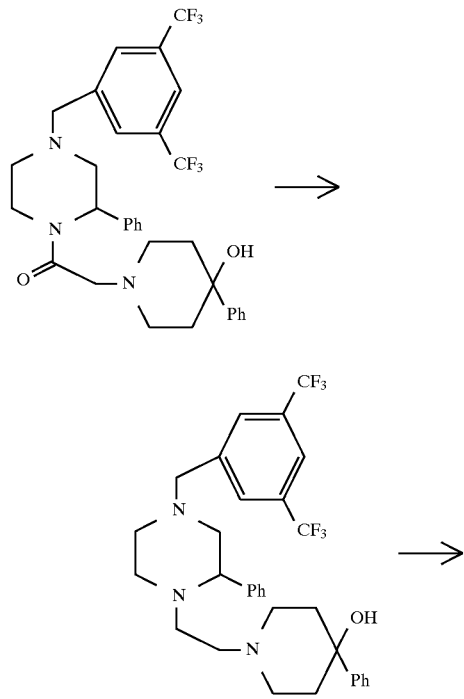

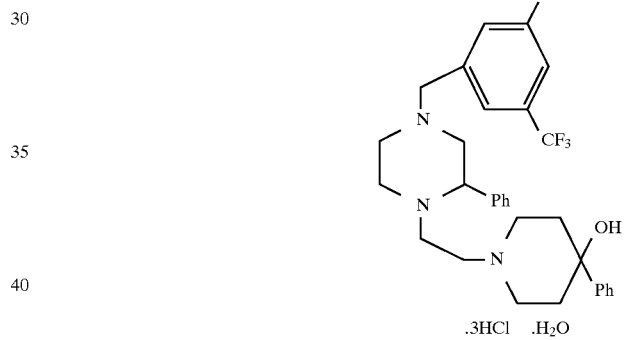

To a solution of (+,−)-4-[[3,5-bis(trifluoromethyl)phenyl]methyl]-1-[2-(4-hydroxy-4-phenyl-1-piperidinyl)acetyl]-2-phenylpiperazine (0.74 g, 1.222 mmol) in THF (18.5 mL) was added 10M $BH_3 \cdot S(CH_3)_2$ (0.85 mL, 8.5 mmol). The mixture was heated in an oil bath at 80° C. under nitrogen overnight. After completion, excess $BH_3$ was decomposed by dropwise addition of MeOH to the cooled solution under nitrogen. MeOH was evaporated and the residue was redissolved in EtOH (22.2 mL). $K_2CO_3$ (0.31 g, 2.69 mmol) was added and the mixture was refluxed at 80° C. for five hours. After TLC showed that the reaction was complete, the solid was filtered off and the filtrate was evaporated under vacuum. The residue was redissolved in EtOAc (200 mL), washed with brine (100 mL) and dried over $MgSO_4$. It was filtered and evaporated under vacuum to give an oil which was purified by flash chromatography on flash grade silica gel (100 g), eluting with 10% $NH_3MeOH/CH_2Cl_2$ to give the desired material as an oil (0.504 g, 0.852 mmol, 69.8%). A portion of the oil (0.35 g) was converted to its hydrochloride salt by dissolving in dry $CH_2Cl_2$ (17.5 mL), followed by the addition of 2.3M HCl-EtOH (0.84 mL). Solvents were removed after stirring at room temperature for 0.25 h and the residue was vacuum dried, m.p. 215°–220° C.; FAB MS [M+1]$^+$ 592.1

Found, C, 53.17; H, 5.51; N, 5.77; Cl, 14.37; F, 15.62. Calcd. for $C_{33}H_{38}N_4F_6.3$ HCl.$H_2O$, C, 53.45; H, 5.61; N, 5.84, Cl, 14.79; F, 15.85.

EXAMPLE 5

By a process analogous to the process described in Examples 2 and 4, employing appropriate heterocyclic derivatives (Z group), listed below, in place of 4-hydroxy-4-phenylpiperidine, the following compounds were prepared.

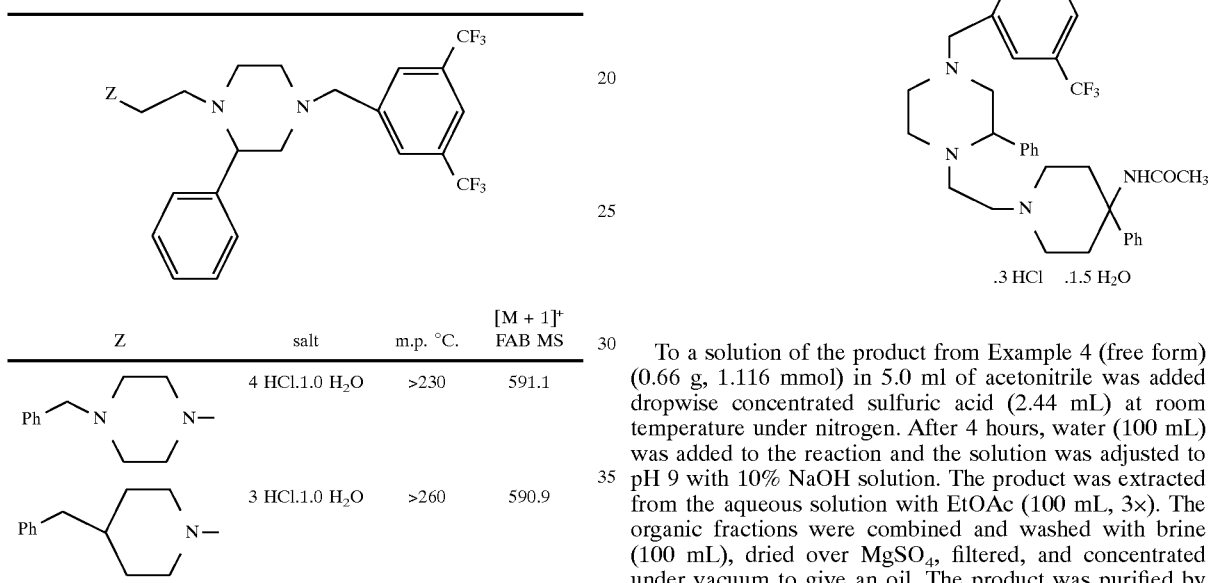

| Z | salt | m.p. °C. | [M + 1]$^+$ FAB MS |
|---|---|---|---|
|  | 4 HCl.1.0 $H_2O$ | >230 | 591.1 |
|  | 3 HCl.1.0 $H_2O$ | >260 | 590.9 |

EXAMPLE 6

Preparation of (+,−)-N-[1-[2-[4-[[3,4-bis(trifluoromethyl)phenyl]methyl]-2-phenyl-1-piperazinyl]ethyl]-4-phenyl-4-piperidinyl]acetamide, trihydrochloride salt, 1.5 hydrate.

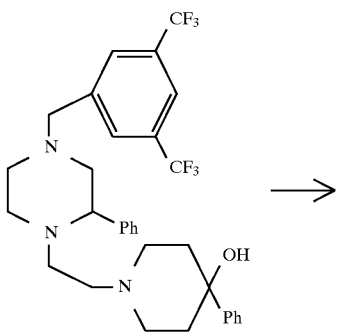

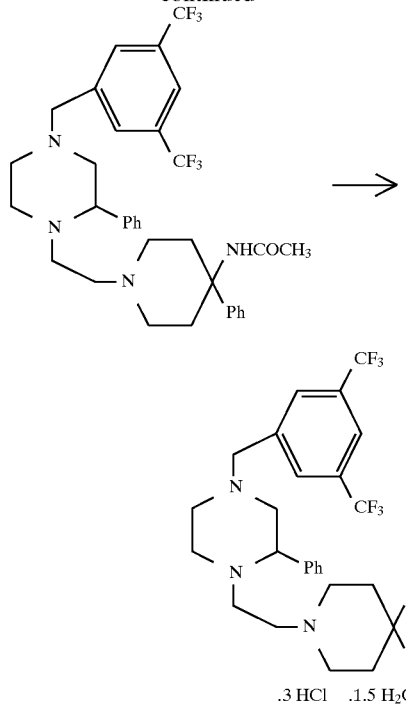

.3 HCl .1.5 $H_2O$

To a solution of the product from Example 4 (free form) (0.66 g, 1.116 mmol) in 5.0 ml of acetonitrile was added dropwise concentrated sulfuric acid (2.44 mL) at room temperature under nitrogen. After 4 hours, water (100 mL) was added to the reaction and the solution was adjusted to pH 9 with 10% NaOH solution. The product was extracted from the aqueous solution with EtOAc (100 mL, 3×). The organic fractions were combined and washed with brine (100 mL), dried over $MgSO_4$, filtered, and concentrated under vacuum to give an oil. The product was purified by flash chromatography on flash silica gel (80 g) and was eluted with 10% $NH_3$-MeOH/$CH_2Cl_2$ to give an oil (0.40 g, 0.774 mmol, 69%). A portion of this oil (0.4 g, 0.632 mmol) was dissolved in $CH_2Cl_2$ (20 ml) and treated with 2.3M HCl-EtOH (2.528 mmol). After stirring at RT for 0.5 h, solvents were removed under vacuum to give a white solid, m.p. 245°–247° C.; FAB MS [M+1]$^+$ 633.4;

Found, C, 53.27; H, 5.80; N, 7.23; Cl, 13.91; F, 14.55. Calcd. for $C_{34}H_{38}ON_4F_6.3$ HCl.1.5 $H_2O$, C, 53.09; H, 5.76; N, 7.28; Cl, 13.83; F, 14.82.

EXAMPLE 7

Preparation of (+,−)-1-[(2-methoxyphenyl)methyl]-3-phenyl-piperazine, dihydrochloride salt.

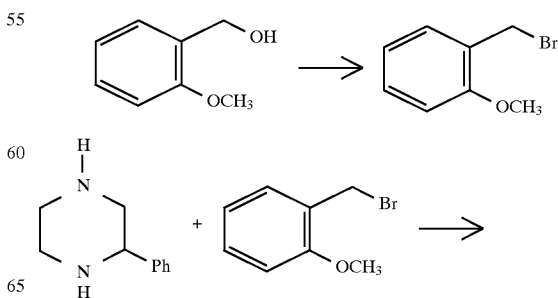

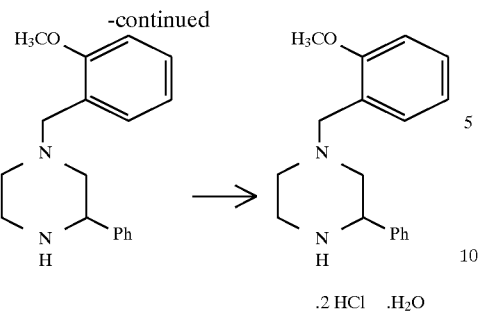
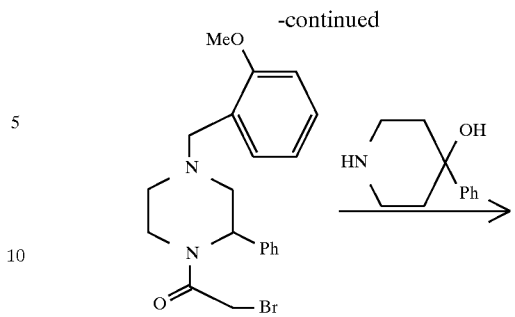

To a solution of 1-hydroxymethyl-2-methoxy-benzene (28.7 g, 0.207 mol) in $CH_2Cl_2$ (574 mL) at 0° C. under nitrogen was added slowly $PBr_3$ (13.66 mL, 0.145 mol). After stirring for an additional 1.5 hours, MeOH (13.66 mL) was added and stirred for 5 minutes. To this mixture was added dropwise 10% $Na_2CO_3$ (2 mL) solution and stirred for 5 minutes. The mixture was then washed with 10% $Na_2CO_3$ (50 mL, 2×) and brine (100 mL). It was dried over $MgSO_4$, and filtered. The filtrate was removed under vacuum to give an oil (40 g) of 1-bromomethyl-2-methoxy-benzene. This material was used without purification.

To a solution of (+,−)-2-phenyl-piperazine (2.83 g, 17.44 mmol) (described in Example 1) in dry $CH_2Cl_2$ (141.5 mL) at −78° C. was added slowly a solution of 1-bromomethyl-2-methoxy-benzene (3.507 g, 17.44 mmol) in dry $CH_2Cl_2$ (35 mL) under nitrogen. The reaction was stirred at −78° C. and gradually warmed to RT overnight. After completion, the product was diluted with $CH_2Cl_2$ (200 mL), washed with brine (100 mL), dried over $MgSO_4$ and filtered. The filtrate was removed under vacuum to give an oil. The product was purified by flash chromatography on flash grade silica gel (150 g), eluting with 4% MeOH/$CH_2Cl_2$ to give the title compound as an oil (2.68 gram, 54%). A portion of this oil (0.33 g, 1.168 mmol) was dissolved in $CH_2Cl_2$ (10.0 mL) and treated with 2.3M HCl (1.1 mL, 2.53 mol). After stirring at room temperature for 10 minutes, solvents were removed under vacuum to give a solid, m.p. 152°–156° C.; FAB MS $[M+1]^+$ 283.2.

Found, C, 58.18; H, 7.23; N, 7.33; Cl, 18.89. Calcd. for $C_{18}H_{22}ON_2$.2 HCl.$H_2O$, C, 57.91; H, 7.02; N, 7.50; Cl, 18.99.

EXAMPLE 8

Preparation of (+,−)-1-[(4-hydroxy-4-phenyl-1-piperidinyl)acetyl]-4-[(2-methoxy-phenyl)methyl]-2-phenyl piperazine, dihydrochloride salt.

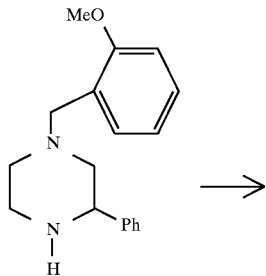

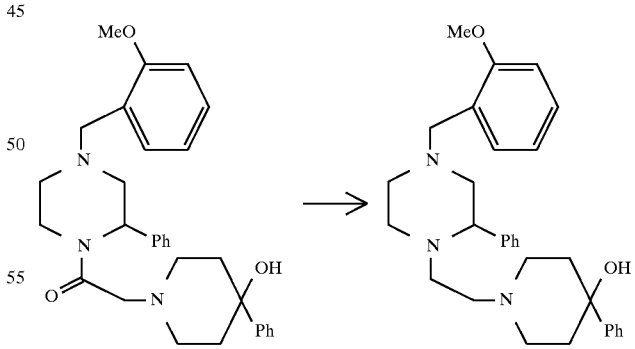

The bromoacetyl derivative of the product from Example 7 was prepared according to the procedure described in Example 2. This intermediate was used for the next reaction without further purification. The title compound was prepared by employing a process analogous to that described in Example 3, via the bromoacetyl derivative of (+,−)-1-[(2-methoxyphenyl)methyl]-3-phenyl-piperazine to give a solid, m.p. 183°–186° C.; FAB MS $[M+1]^+$ 500;

Found, C, 61.30; H, 7.54; N, 6.98; Cl, 11.65. Calcd. for $C_{31}H_{37}N_3O_3$.2 HCl, C, 61.18; H, 7.12; N, 6.90; Cl, 11.65.

EXAMPLE 9

Preparation of (+,−)-1-[2-[4-[(2-methoxyphenyl)methyl]-2-phenyl-1-piperazinyl]ethyl]-4-phenyl-4-piperidinol.

The product from Example 8 (free form) (0.7 gram, 1.4 mmol) was used to prepare the title compound by employing a procedure analogous to the procedure for Example 4. The title compound was a solid, m.p. 63°–65° C.; FAB MS $[M+1]^+$ 486;

Found, C, 75.86; H, 8.52; N, 8.54. Calcd. for $C_{31}H_{39}N_3O_2$, C, 75.54; H, 8.14; N, 8.53.

EXAMPLE 10

Preparation of 2-(3,4-dichlorophenyl)piperazine

A. Synthesis:

METHOD 1

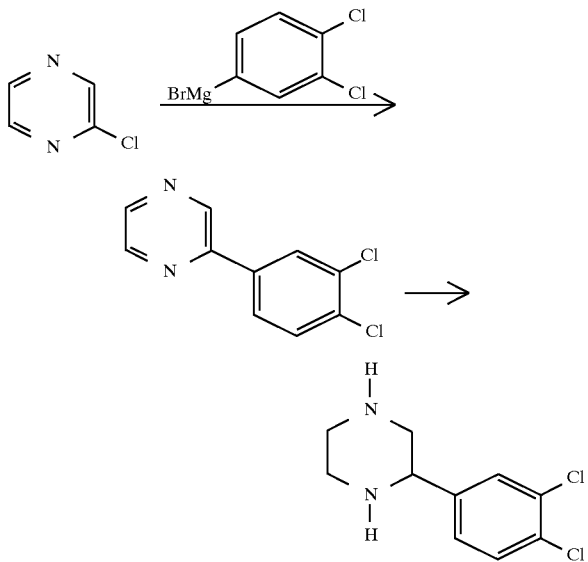

2-(3,4-Dichlorophenyl)pyrazine was prepared according to the analogous method described in Example 1. m.p. 118°–119° C.; FAB MS [M+1]+ 35 Cl 225.

To a solution of 2-(3,4-dichlorophenyl)pyrazine (10 g, 44.43 mmol) in dry THF (150 mL) was added slowly a solution of DIBAL-H (1M in THF, 444.3 mL) through a dropping funnel at 10° C. under $N_2$. The color of solution turned into red wine at the end of addition. The solution was gradually warmed up to room temperature overnight. After completion (checked by TLC) the reaction was quenched slowly by the addition of saturated $Na_2SO_4$ solution until no more $H_2$ evolved. White precipitate was formed after stirring for 1.0 h. The precipitate was filtered off, rinsed with THF, dried over $MgSO_4$ and evaporated to dryness. The crude material (10 g) was purified by flash chromatography on 300 g of flash grade silica gel in 7.5% $NH_3$-MeOH/$CH_2Cl_2$ to give 4.11 g (17.77 mmol, 40%) of 2-(3,4-dichloro-phenyl)piperazine. m.p. 74°–76° C.; FAB MS [M+1]+ 231.

METHOD 2

2-(3,4-Dichlorophenyl)piperazine was also synthesized according to the method published in J.Med.Chem. 9,181, 1966.

General method for the synthesis of 2-aryl-piperazine derivatives.

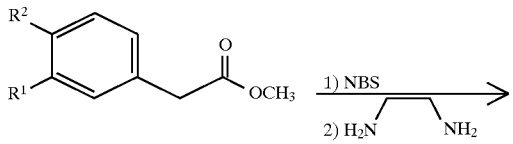

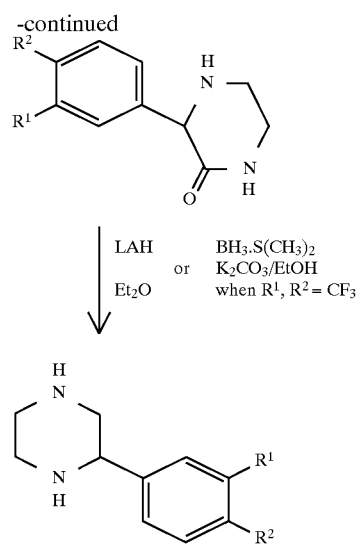

$R^1$ = Cl, H or other substituents i.e. $OCH_3$, $CF_3$, Br, I, F, etc.

$R^2$ = Cl, H or other substituents i.e. $OCH_3$, $CF_3$, Br, I, F, etc.

B. Resolution of 2-(3,4-dichlorophenyl)piperazine

Step 1

A solution of 2-(3,4-dichlorophenyl)piperazine (36.05 g, 0.156 mol) in methanol (200 mL) was treated with a solution containing two equivalents of N-acetyl-L-leucine (54.02 g, 0.312 mol) and heated until all of the material was dissolved. EtOAc (2.2 L) was added to this solution and allowed to stand at ambient temperature overnight. The solvent phase was decanted from the precipitated salt and concentrated in vacuo. This procedure was repeated using 37.88 g of 2-(3, 4-dichlorophenyl)piperazine (0.164 mol) and 56.68 g of N-acetyl-L-leucine (0.327 mol).

Step 2

The concentrated salts from both solvent phases in step 1 were combined and heated in methanol (550 mL) until all of the material dissolved. EtOAc (2.75 L) was added to this solution and allowed to stand at ambient temperature overnight. The solvent phase was decanted from the precipitated salt and concentrated in vacuo to give ~95 g of piperazine salt (72% ee of enantiomer A).

Step 3

The salt from the solvent phase in step 2 was dissolved in a solution of $H_2O$ (800 mL) and aq. ammonia (400 mL) and extracted with $CH_2Cl_2$ (4×400 mL). The combined organic layers were dried with $MgSO_4$ and concentrated to give 37 g of the piperazine free base. The free base was successively recrystallized from hexane (890, 600 and 450 mL) to give 16 g of piperazine (>99.9% ee of enantiomer A). $[\alpha]D^{24.7°}$ C.=−45.0° (MEOH)

Step 4

The precipitated salts from step 1 were combined and heated in methanol (220 mL) until all of the material dissolved. EtOAc (2.2 L) was added to this solution and allowed to stand at ambient temperature overnight. The solvent phase was decanted from the precipitated salt and dried in vacuo to give ~43 g of piperazine salt (93% ee of enantiomer B).

Step 5

A 12.3 g portion of salt (75% ee of enantiomer B) prepared an analogous procedure to that in step 4 was dissolved in 0.5M NaOH (400 mL) and extracted with $CH_2Cl_2$ (4×155 mL). The combined organic layers were dried with $MgSO_4$ and concentrated to give 3.72 g of the piperazine free base. The free base was successively recrystallized from hexane (90 and 70 mL) to give 2.1 g of piperazine (98% ee of enantiomer B).

EXAMPLE 11

By procedures analogous to the procedures described in Examples 1, 2 and 10 but using (+,−)-1-[[3,5-bis(trifluoromethyl)phenyl]methyl]-3-(3,4-dichlorophenyl)-piperazine in place of (+,−)-1-[[3,5-bis(trifluoromethyl)phenyl]methyl]-3-phenyl-piperazine, and employing appropriate heterocyciic reagents (Z group), listed below, the following compounds were prepared.

| Z | m.p °C. | [M + 1]+ FABMS based on 35Cl | [M + 1]+ High Res. MS |
|---|---|---|---|
| Ph, H₃CC—N(H)— (piperidinyl)N— with O= | free form 108–110 | | Cal'd 715.2041 Found 715.2050 |
| Ph—CH₂—N(piperazinyl)N— | 2 H₂O 58–60 | | Cal'd 673.1936 Found 673.1935 |
| Ph—CH₂—(piperidinyl)N— | free form 55–57 | 672 | |
| (2,6-dimethylphenyl)—N(piperazinyl)N— | free form 74–76 | 687 | |
| MeO, PhS(=O)—(piperidinyl)N— | free form 82–83 | 750 | |
| Ph, H₂N—C(=O)—(piperidinyl)N— | free form 105–107 | 702 | |
| HO, Ph—(piperidinyl)N— | free form 85–86 | 674 | |

EXAMPLE 12

Preparation of (+,−)-1-[2-[4-[[3,5-bis(trifluoromethyl)phenyl]methyl]-2-(3,4-dichlorophenyl)-1-piperazinyl]ethyl]-4-phenyl-4-piperidinol.

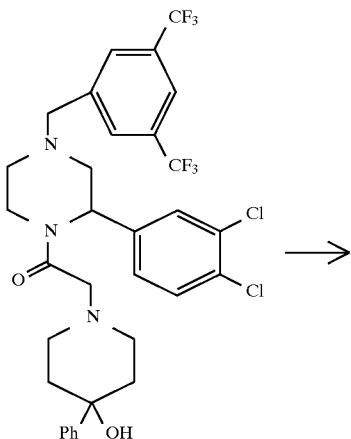

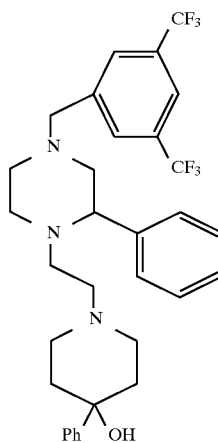

By a procedure analogous to the procedure described in Example 4, using the last compound from Example 11, as a starting material, the title compound was prepared in 67% yield as a solid, m.p. 71°–72° C.; FAB MS [M+1]+ 660;

Found, C, 58.08; H, 5.14; N, 6.40; F, 17.37. Calcd. for $C_{32}H_{33}N_3Cl_2F_6O$, C, 58.19; H, 5.04; N, 6.36; F, 17.26.

EXAMPLE 13

Preparation of (+,−)-[3,5-bis(trifluoromethyl)benzoyl]-3-(3,4-dichlorophenyl)piperazine

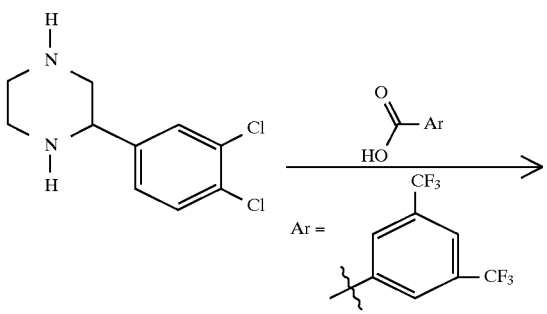

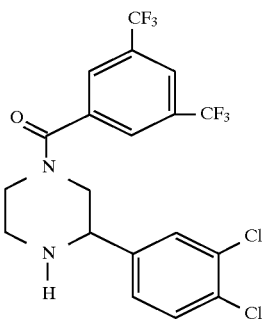

To a cooled solution of $CH_2Cl_2$ (103 mL) containing 2-(3,4-dichlorophenyl)piperazine (1.15 g 5.0 mmol), 3,5-bis-(trifluoromethyl)benzoic acid (1.34 g, 5.09 mmol), and N-hydroxybenzotriazole monohydrate (0.688 g, 5.09 mmol) at −20° C. were added $Et_3N$ (0.711 mL 5.09 mmol) and N,N-dimethylaminopropyl-ethylcarbodimide (DEC) (0.967 g, 5.09 mmol) under nitrogen. The reaction was kept at −20° C. for an hour and gradually warmed to RT overnight. After stirring 20 h, the reaction was complete and $CH_2Cl_2$ (200 mL) was added. The organic solution was washed with 5% $NaHCO_3$ (80 mL) and brine (80 mL, 2×), dried over $MgSO_4$, filtered and concentrated under vacuum to give 2.1 g of crude product. The product was purified by flash chromatography on flash grade silica gel (120 g), eluting with 2% $NH_3$-MeOH/$CH_2Cl_2$ to give a foam solid (1.25 g, 2.65 mmol, 53%). m.p. 50°–53° C.; FAB MS [M+1]+ 470.9;

Calcd. for $C_{19}H_{14}ON_2F_6Cl_2$, C, 48.42; H, 2.99; N, 5.94; F, 24.19; Cl, 15.05; Found, C, 48.57; H, 2.90; N, 5.94; F, 23.90; Cl, 15.03.

EXAMPLE 14

Preparation of (+,−)-4-[3,5-bis(trifluoromethyl)benzoyl]-2-(3,4-dichlorophenyl)-1-[[(4-hydroxy-4-phenyl-1-piperidinyl)]acetyl]piperazine.

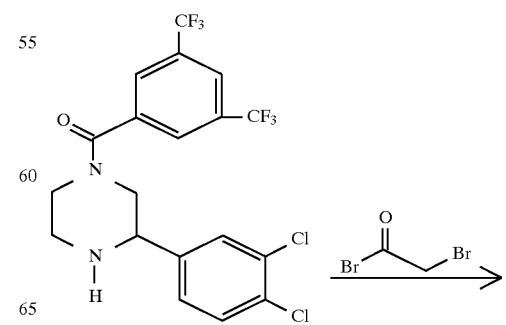

71

-continued

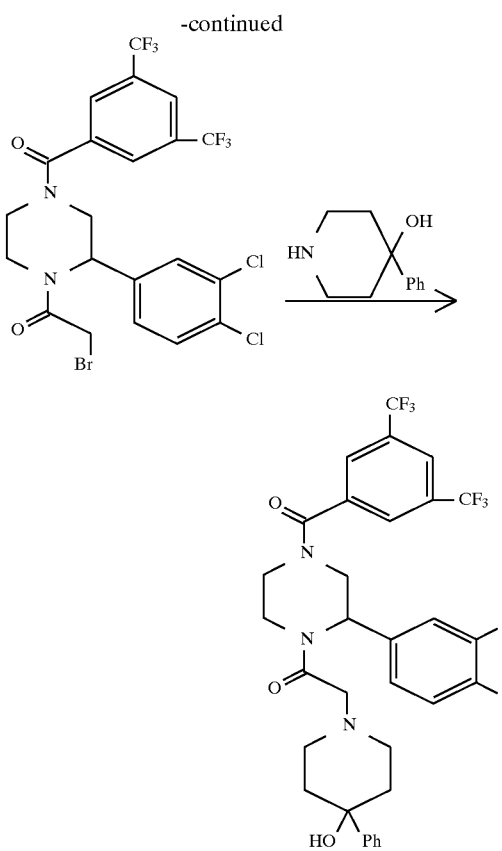

72

To a solution of (+,−)-[3,5-bis(trifluoromethyl)benzoyl]-3-(3,4-dichlorophenyl)piperazine (0.6 g, 1.274 mmol) in dry $CH_2Cl_2$ (12.0 mL) at −78° C. was added diisopropylethylamine (0.266 mL, 1.53 mmol) followed by the dropwise addition of bromoacetyl bromide (0.124 mL, 1.40 mmol). After stirring at −78° C. for 3.5 h under nitrogen, additional diisopropyl ethylamine (0.234 mL, 1.342 mmol) and 4-amino-1-benzyl piperidine (0.279 mL, 1.342 mmol) were added at −78° C. The reaction was gradually warmed to RT overnight. After the reaction was complete, the reaction was diluted with $CH_2Cl_2$ (200 mL), washed with brine (80 mL, 3×) and dried over $MgSO_4$. After filtration, the solvent was removed under vacuum to give a light yellow solid which was purified by flash chromatography on flash grade silica gel (150 g), eluting with 5% $NH_3$-MeOH/$CH_2Cl_2$ to give the title compound was prepared in 72% yield as a solid, m.p. 104°–106° C., FAB MS $[M+1]^+$ 688.1 Calcd. for $C_{32}H_{29}N_3O_3F_6Cl_2$.0.25 $H_2O$, C, 55.45; H, 4.30; N, 6.06; F, 16.45; Cl, 10.23; Found, C, 55.40; H, 4.38; N, 6.05; F, 16.83; Cl, 10.63.

EXAMPLE 15

By employing methods analogous to those described in Example 13 and Example 14 using appropriate alkylation reagents, the following compounds were obtained according to the schemes shown below.

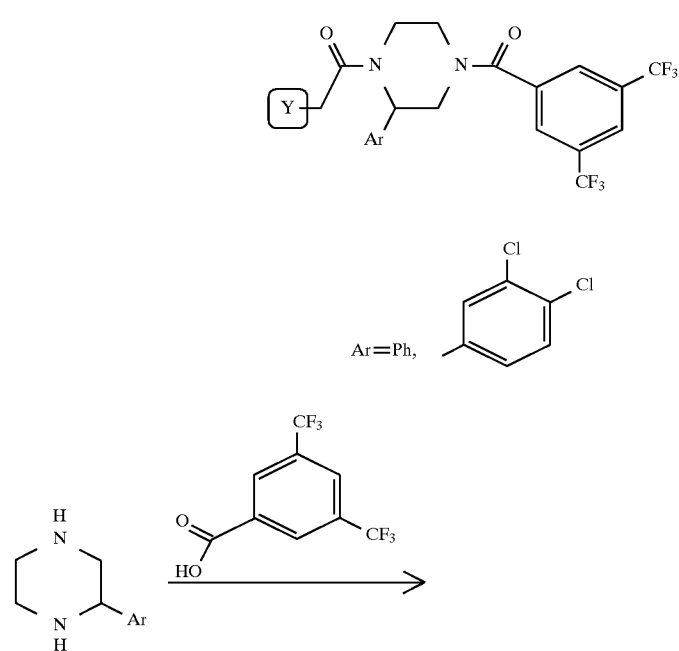

-continued
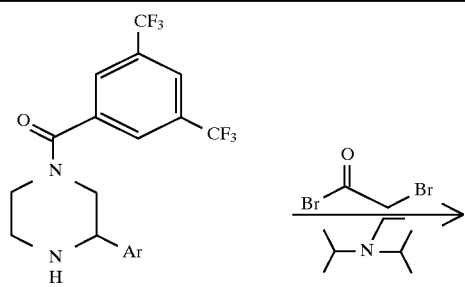
2
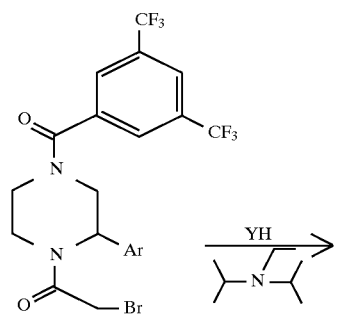
3
purified at this stage
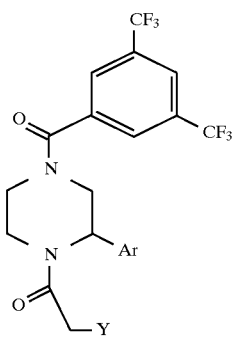
FAB MS [M + 1]+
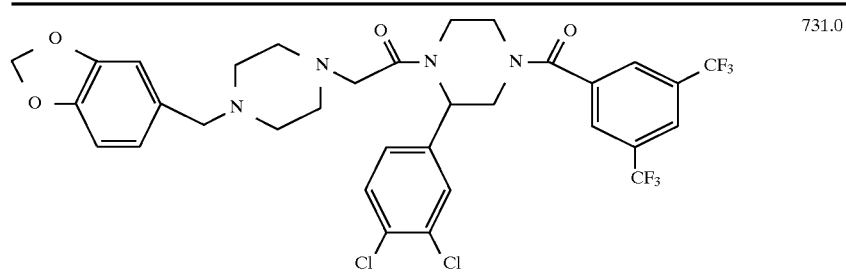
731.0
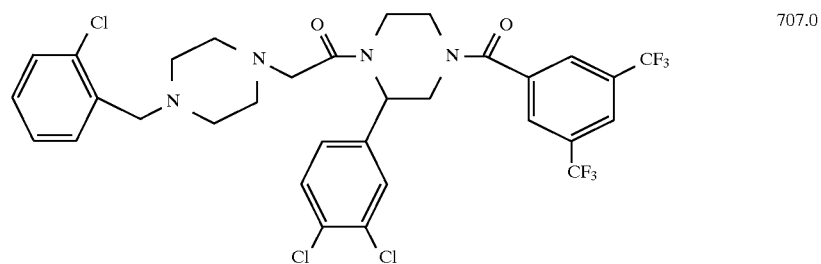
707.0

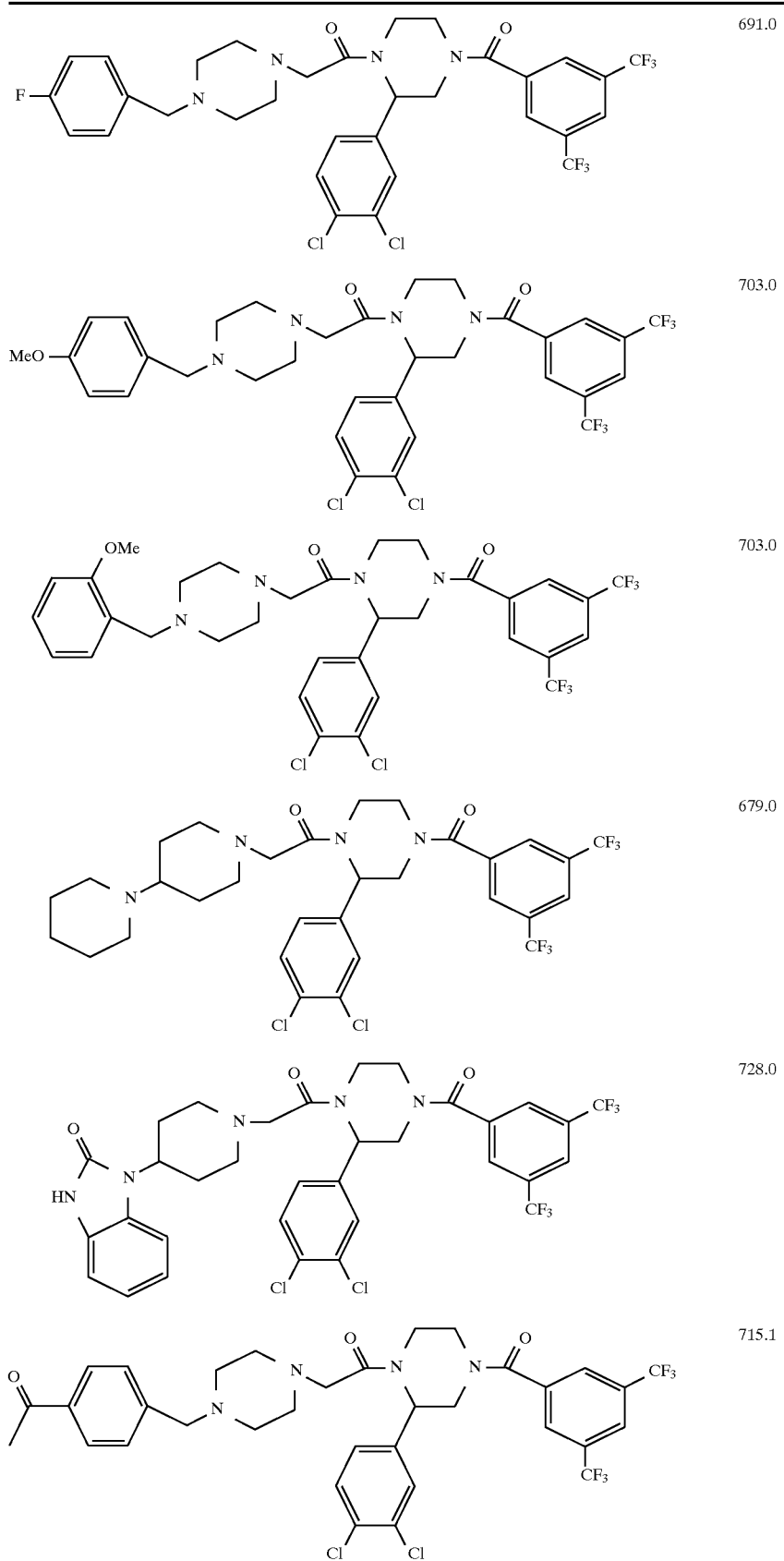
691.0
703.0
703.0
679.0
728.0
715.1

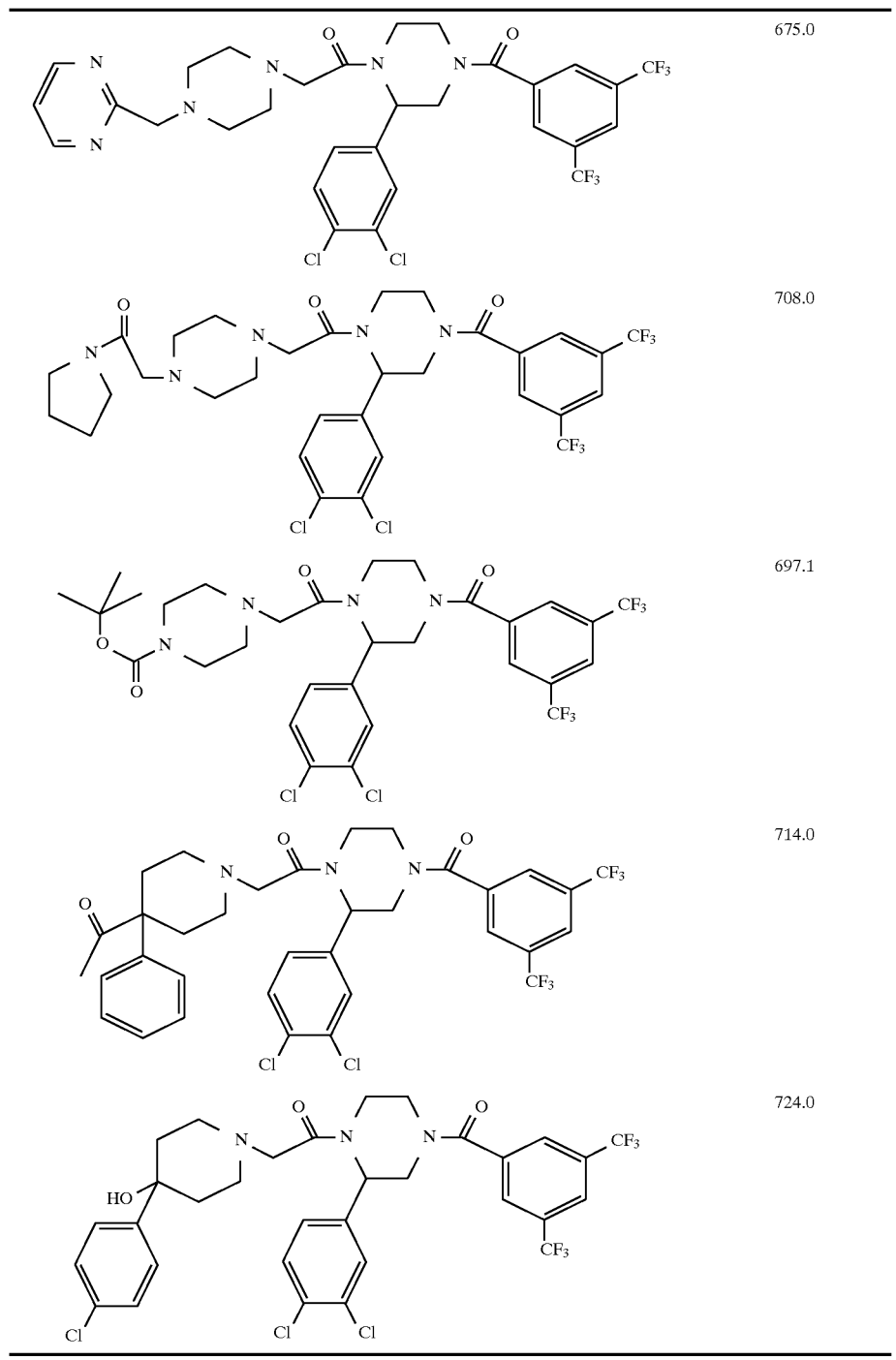

EXAMPLE 16

Preparation of (+,−)-2-(3,4-dichlorophenyl)-4-(2-methoxybenzoyl)-1-[[(4-hydroxy-4-phenyl-1-piperidinyl)]acetyl]piperazine By employing methods analogous to those described in Example 13 and Example 15 and using 2-methoxybenzoic acid in place of bis(3,5-trifluoromethyl) benzoic acid the title compound was prepared in 71% yield as a solid, m.p. 112°–114° C., FAB MS [M+1]$^+$ 582.0.

EXAMPLE 17

Preparation of (+,−)-4-[3,5-bis(trifluoromethyl)benzoyl]-2-phenyl-1-[[(4-hydroxy-4-phenyl-1-piperidinyl))]acetyl]piperazine.

By employing methods analogous to those described in Example 13 and Example 15, and using 2-phenylpiperazine in place of 2-(3,4-dichlorophenyl)-piperazine the title compound was prepared in 90% yield as a solid:

m.p. 101°–102° C., FAB MS [M+1]$^+$ 620.4; Calcd. for $C_{32}H_{29}N_3O_3F_6Cl_2 \cdot 0.25\ H_2O$, C, 61.57; H, 5.09; N, 6.73; F, 18.27; Found, C, 61.41; H, 5.08; N, 6.71; F, 18.28.

EXAMPLE 18

Preparation of (+,−)-[3,5-dimethylbenzoyl]-3-(3,4-dichlorophenyl)piperazine

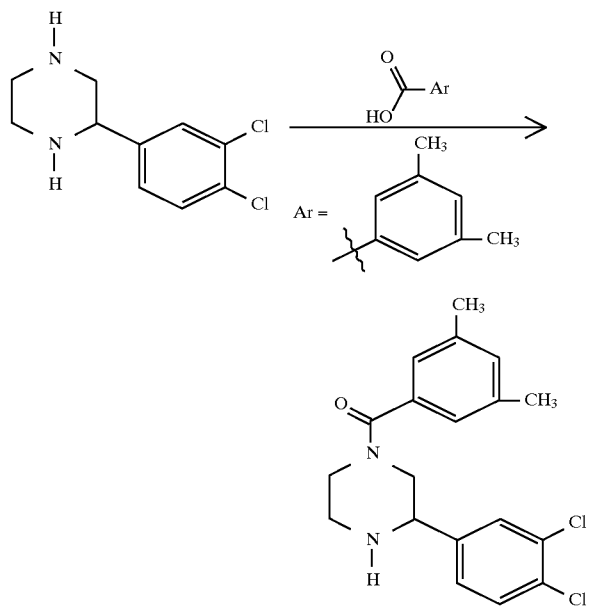

To a cooled solution of CH$_2$Cl$_2$ (600 mL) containing 2-(3,4-dichlorophenyl)piperazine (6.934 g, 30 mmol), 3,5-dimethylbenzoic acid (4.55 g, 30 mmol), and N-hydroxybenzotriazole monohydrate (4.05 g, 30 mmol) at −20° C. were added Et$_3$N (4.2 mL, 30 mmol) and N,N-dimethylaminopropylethylcarbodimide (DEC) (5.86 g, 30 mmol) under nitrogen. The reaction was kept at −20° C. for an hour and gradually warmed to RT overnight. After stirring 22 h, the reaction was complete and CH$_2$Cl$_2$ (200 mL) was added. The organic solution was washed with brine (150 mL, 3×), dried over MgSO$_4$, filtered and concentrated under vacuum to give 8.2 g of crude product. The product was crystallized from CH$_2$Cl$_2$/Hexane to give a light yellow solid (6.3 g, 17.34 mmol, 57.8%), m.p. 139°–141° C.; FAB MS [M+1]$^+$ 363.1.

EXAMPLE 19

Preparation of (+)-[3,5-dimethylbenzoyl]-3-(3,4-dichlorophenyl)piperazine (Enantiomer B)

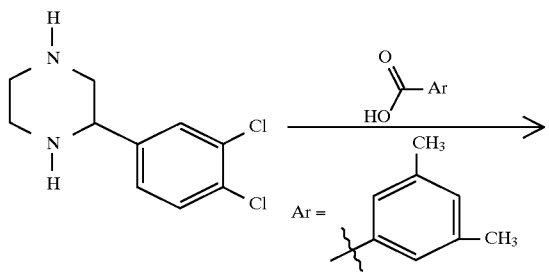

-continued
(Enantiomer B)

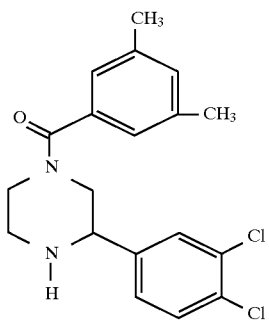

The title compound was prepared by an analogous method to that described in Example 18 using (−)-2-(3,4-dichlorophenyl)piperazine in place of (+,−)-2-(3,4-dichlorophenyl)piperazine, m.p. 97°–100° C.;
[α]$_D^{22.5°\ C.}$=+87.2° (MeOH); FAB MS [M+1]$^+$=363.1

EXAMPLE 20

Preparation of 4-[3,5-bis(trifluoromethyl)benzoyl]-2-(3,4-dichlorophenyl)-1[1,2-dioxo-2-[4-(phenylmethyl)-1-piperazinyl]ethyl]piperazine

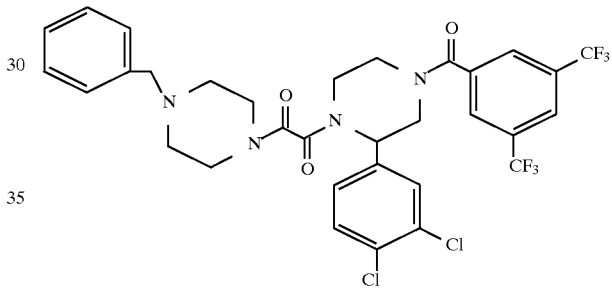

Step 1 A solution of 1-benzylpiperazine (1.75 mL, 10 mmol) in CH$_2$Cl$_2$ (60 mL) was treated with methyl acrylate (0.90 mL, 10 mmol) at ambient temperature for 2 days. The reaction mixture was concentrated to give a clean Michael product (2.6 g, 10 mmol, 100%).

Step 2 A solution of the product from step 1 (0.92 g, 3.5 mmol) in methanol (10 mL) was treated with 1M LiOH (5.2 mL, 5.2 mmol) for 1 h. The reaction mixture was concentrated in vacuo at 50° C. and the residue was suspended in CH$_2$Cl$_2$ (25 mL), filtered and concentrated to obtain 0.72 g of the desired acid (2.9 mmol, 83%).

Step 3 A solution of the product from step 2 (0.72 g, 2.9 mmol) in benzene (12 mL) was treated with oxayl chloride (300 mL, 3.4 mmol) and DMF (1 drop) at 0° C. The reaction mixture was warmed up to ambient temperature and stirred for 90 min. The reaction mixture was concentrated in vacuo and the residue was suspended in CH$_2$Cl$_2$ (20 mL). To this suspension were added 1-[3,5-bis(trifluoro-methyl)benzoyl]-3-(3,4-dichlorophenyl)piperazine (1.4 g, 2.9 mmol) in CH$_2$Cl$_2$ (14 mL) and triethylamine (0.80 mL, 5.7 mmol). The reaction mixture was stirred for 1 h and H$_2$O (100 mL) was added. The mixture was extracted with CH$_2$Cl$_2$ (50 and 25 mL). The combined organic layers were washed with brine (50 mL), dried (MgSO$_4$) and concentrated. The crude material was purified by silica gel chromatography, eluanting with CH$_2$Cl$_2$:methanol (50:1)) to obtain 0.64 g (0.91 mmol, 31%) of the titled compound as a colorless foam.

HRMS (FAB, M+H$^+$): m/e calc'd for [C$_{32}$H$_{29}$Cl$_2$F$_6$N$_4$O$_3$]$^+$: 701.1521, found 701.1513.

EXAMPLE 21

Preparation of 1-[3,5-dimethylbenzoyl]-3-(3,4-dichlorophenyl)piperazine (enantiomer B)

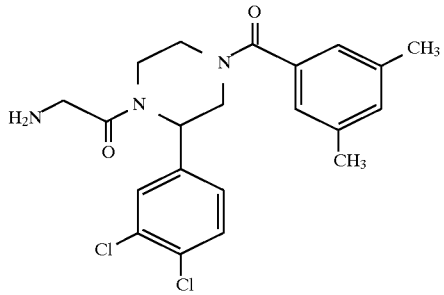

To a solution of BOC glycine (0.918 g, 5.24 mmol), (+)-(3,5-dimethylbenzoyl)-3-(3,4-dichlorophenyl) piperazine (enantiomer B)(1.80 g, 4.95 mmol) (prepared in Example 19), DEC (0.983 g, 5.13 mmol), HOBT (0.687 g, 5.07 mmol) and Hünig's base (0.92 mL, 5.1 mmol) in $CH_2Cl_2$ (100 mL) was left stirring for 2.5 d. The reaction mixture was added to $CH_2Cl_2$ (200 mL) and washed with sat. $NaHCO_3$ (3×100 mL), brine (100 mL), dried with $MgSO_4$ and concentrated. The crude material was treated with MeOH saturated HCl (25 mL) for 10 h and concentrated. The resulting residue suspended in 0.3N NaOH (150 mL) and extracted with $CH_2Cl_2$, (3×50 mL). The combined organic layers were washed with brine (50 mL), dried with $MgSO_4$, concentrated, and purified by flash chromatography on silica gel, eluting with 20:1:0.2 $CH_2Cl_2$/MeOH/conc. aq. $NH_3$ to give 0.95 g of the titled product as a white solid. HRMS (FAB, M+H$^+$); m/e calc'd $[C_{31}H_{24}Cl_2N_3O_2]^+$: 420.1246 found 420.1254.

EXAMPLE 22

Preparation of 2-(3,4-dichlorophenyl)-4-(3,5-dimethylbenzoyl)-1-[[(4-carbethoycyclohexyl) amino]acetyl]piperazine (enantiomer B)

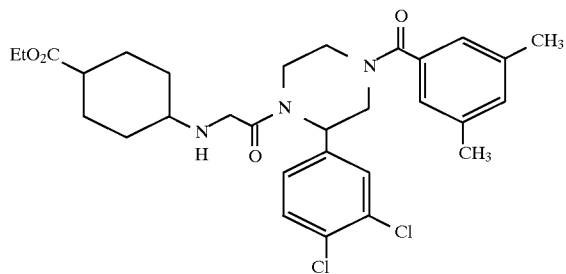

A $CH_2Cl_2$ (2.0 mL) solution containing the amino compound from Example 21 (0.10 g, 0.23 mmol) and 1-carbethoxy-4-piperidone (39 mg, 0.23 mmol) was treated with $NaBH(OAc)_3$ (63 mg, 0.32 mmol) and acetic acid (15 mL, 0.26 mmol) and left stirring overnight. The reaction mixture was quenched with 1N NaOH and extracted with $CH_2Cl_2$ (50 mL,3×). The combined organic layers were washed with brine, dried with $MgSO_4$ and chromatographed on silica gel eluting with 5% $NH_3$ sat. MeOH/$CH_2Cl_2$ to give 46 mg of the titled product as a white solid. HRMS (FAB, M+H$^+$); m/e calc'd $[C_{30}H_{38}Cl_2N_3O_4]^+$: 574.2239, found 574.2250.

EXAMPLE 23

Preparation of 2-(3,4-dichlorophenyl)-4-(3,5-dimethylbenzoyl)-1-[[(3-methylcyclohexyl) amino) acetyl]piperazine (diasteromers from enantiomer B)

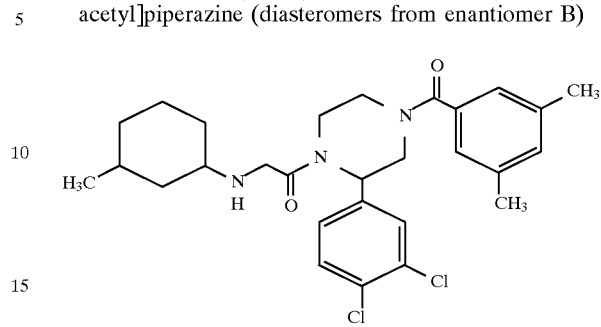

By employing method analogous to that described in Example 22 using 3-methylcyclohexanone, the title compound was obtained. HRMS (FAB, M+H$^+$); m/e calc'd $[C_{28}H_{36}Cl_2N_3O_2]^+$: 516.2185, found 516.2199.

EXAMPLE 24

Preparation of 1-[(cyclohexylamino)acetyl]-2-(3,4-dichlorophenyl)-4-(3,5-dimethylbenzoyl) piperazine (enantiomer B)

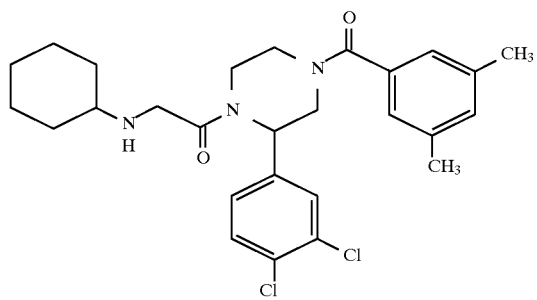

By employing method analogous to that described in Example 22 using cyclohexanone, the title compound was obtained. HRMS (FAB, M+H$^+$); m/e calc'd $[C_{27}H_{34}Cl_2N_3O_2]^+$: 502.2028, found 502.2025.

EXAMPLE 25

Preparation of 1-[(cycloheptylamino)acetyl]-2-(3,4-dichlorophenyl)-4-(3,5-dimethylbenzoyl) piperazine (enantiomer B)

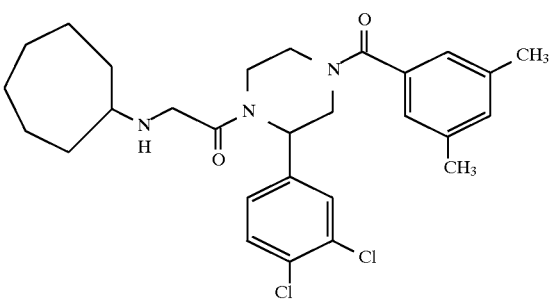

By employing method analogous to that described in Example 22 using cycloheptanone, the title compound was obtained. HRMS (FAB, M+H⁺); m/e calc'd [$C_{28}H_{36}Cl_2N_3O_2$]⁺: 516.2185, found 516.2177.

EXAMPLE 26

Preparation of 1-[[(4-cyano-4-phenylcyclohexyl) amino]acetyl-2-(3,4-dichlorophenyl)-4-(3,5-dimethylbenzoyl)piperazine (enantiomer B)

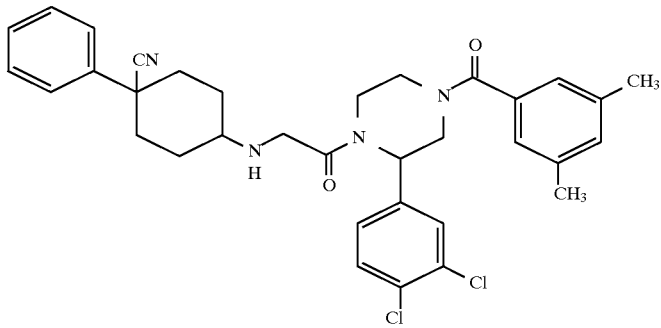

By employing method analogous to that described in Example 22 using 4-cyano-4-phenylcyclohexanone, the title compound was obtained. HRMS (FAB, M+H⁺); m/e calc'd [$C_{34}H_{37}Cl_2N_4O_2$]⁺: 603.2294, found 603.2271.

EXAMPLE 26

Preparation of (+/−)-2-(3,4-dichlorophenyl)-4-(3,5-dimethylbenzoyl)-1-[[(4-phenylcyclohexyl] amino] acetyl]-piperazine

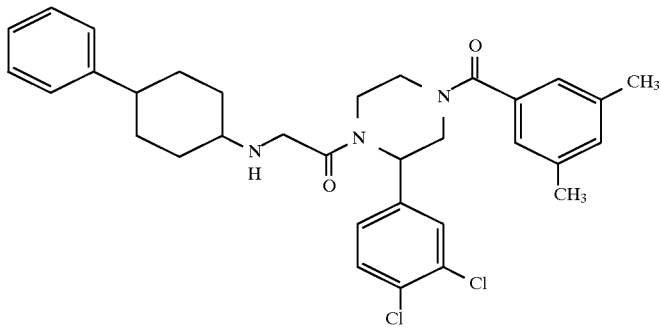

By employing methods analogous to that described in Examples 21 and 22 using the (+,−)-(3,5-dimethylbenzoyl)-3-(3,4-dichlorophenyl)piperazine (enantiomer B) from example 18 and 4-phenylcyclohexanone, the title compound was obtained. HRMS (FAB, M+H⁺); m/e calc'd [$C_{33}H_{39}Cl_2N_3O_2$]⁺: 578.2341, found 578.2327.

EXAMPLE 27

Preparation of 2-(3,4-dichlorophenyl)-4-(3,5-dimethylbenzoyl)-1-[3-[4-(2-keto-1-benzimidazolinyl)piperidinyl]-1-oxopropyl] piperazine (enantiomer B)

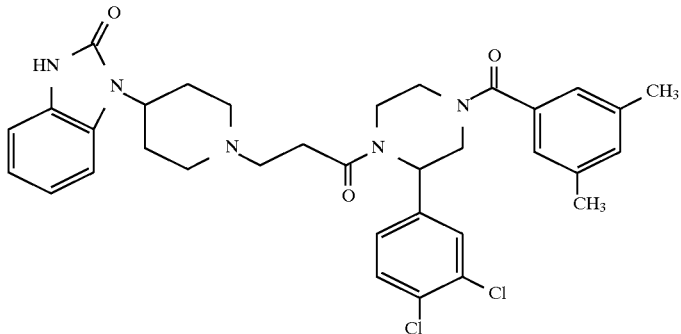

A cooled CH$_2$Cl$_2$ (4 mL) solution containing (+)-(3,5-dimethylbenzoyl)-3-(3,4-dichlorophenyl)piperazine (enantiomer B) from Example 19 (153 mg, 0.42 mmol) and Hünig's base (0.12 mL, 0.86 mmol) at −78° C. was treated with 3-chloropropionyl chloride (0.040 mL, 0.42 mmol) and warmed to RT for 1 h. The reaction mixture was then concentrated in vacuo and resuspended in acetonitrile (2 mL). To the reaction mixture was added 4-(2-keto-1-benzimiaxolinyl)piperidine (104 mg, 0.48 mmol) and left heating overnight at 70° C. The reaction mixture was concentrated and purified by silica gel chromatography, eluting with 20:1:0.1 CH$_2$Cl$_2$/MeOH/conc. aq. NH$_3$ to give 104 mg of the title compound as a white solid (39% yield). HRMS (FAB, M+H$^+$); m/e calc'd [C$_{34}$H$_{38}$Cl$_2$N$_5$O$_3$]$^+$: 634.2352, found 634.2351.

EXAMPLE 28

Preparation of 2-(3,4-dichlorophenyl)-4-(3,5-dimethylbenzoyl)-1-[3-[4-(phenylmethyl)-1-piperidinyl]-1-oxopropyl]piperazine (enantiomer B)

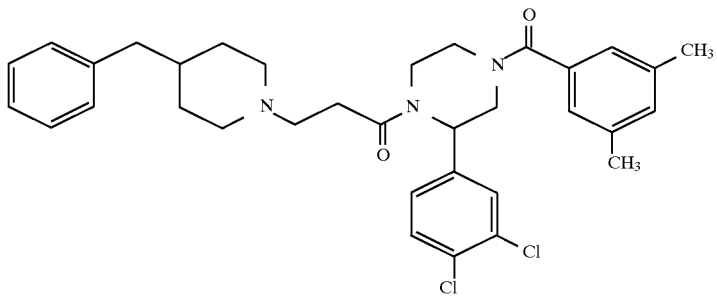

By employing method analogous to that described in Example 27 using 4-benzylpiperidine, the title compound was obtained. HRMS (FAB, M+H$^+$); m/e calc'd [C$_{34}$H$_{40}$Cl$_2$N$_3$O$_2$]$^+$: 592.2498, found 592.2494.

EXAMPLE 29

Preparation of 2-(3,4-dichlorophenyl)-4-(3,5-dimethylbenzoyl)-1-[1-oxo-3-[4-(phenylmethyl)-1-piperidinyl]propyl]piperazine (enantiomer B)

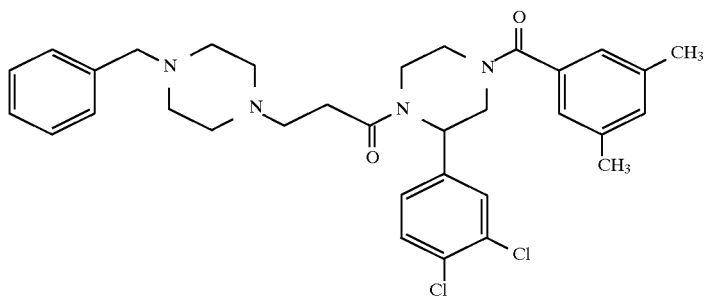

By employing method analogous to that described in Example 27 using 1-benzyl-piperazine, the title compound was obtained. HRMS (FAB, M+H$^+$); m/e calc'd [C$_{33}$H$_{49}$Cl$_2$N$_4$O$_2$]$^+$: 593.2450, found 593.2464.

EXAMPLE 30

Preparation of 2-(3,4-dichlorophenyl)-4-(3,5-dimethylbenzoyl)-1-[3-[4-hydroxy-4-phenyl-1-piperidinyl]-1-oxopropyl]piperazine (enantiomer B)

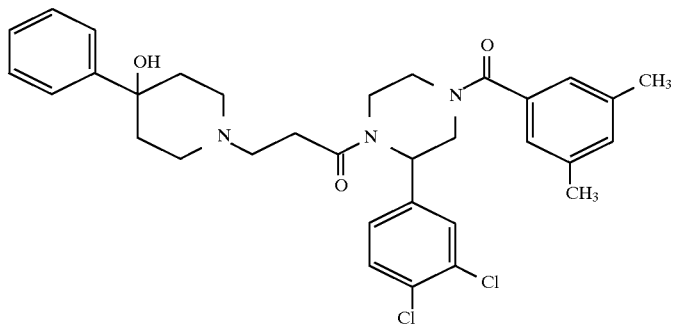

By employing method analogous to that described in Example 27 using 4-hydroxy-4-phenylpiperidine, the title compound was obtained. HRMS (FAB, M+H$^+$); m/e calc'd [C$_{33}$H$_{38}$Cl$_2$N$_3$O$_3$]$^+$: 594.2290, found 594.2285.

What is claimed is:
1. A compound selected from the group consisting of

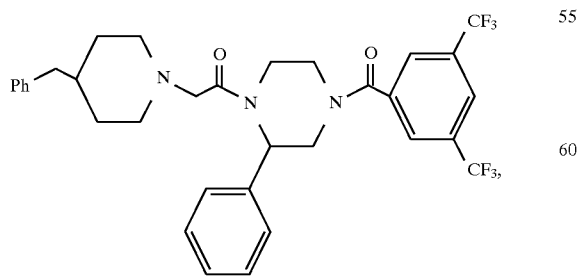

-continued

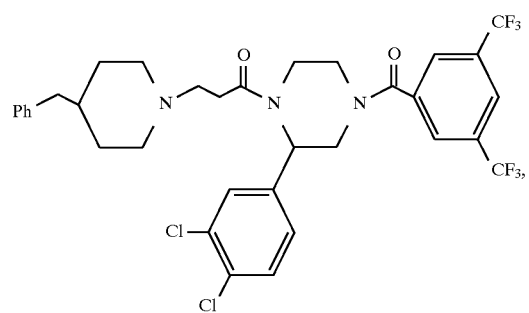

-continued
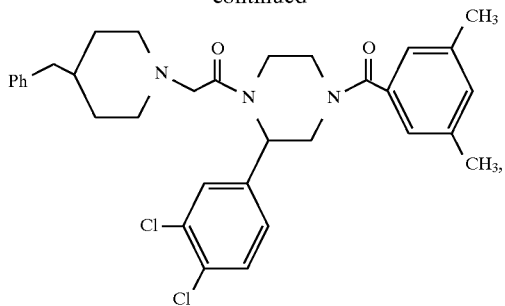
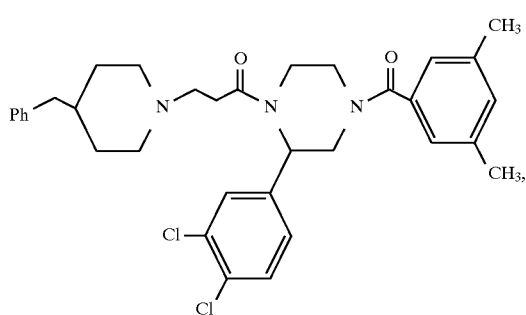
or a compound selected from the group consisting of
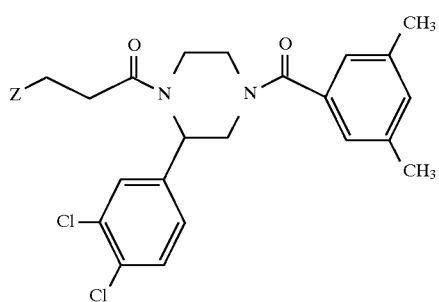
wherein Z is
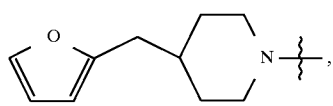
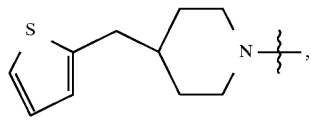
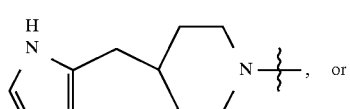
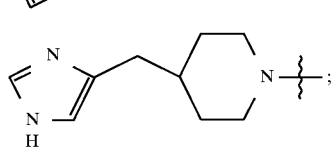
or a compound selected from the group consisting of
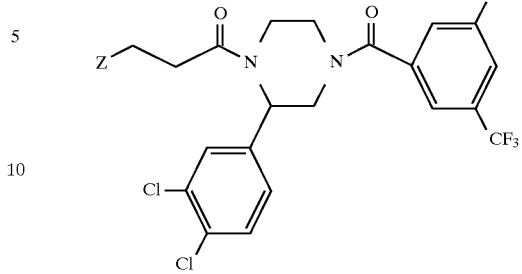
wherein Z is
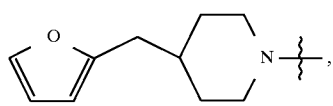
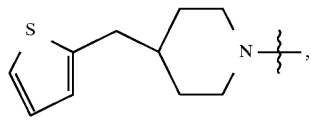
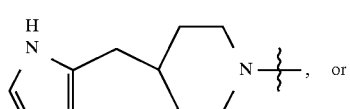
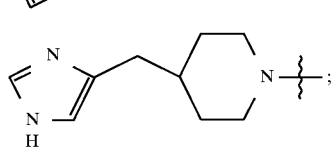
or a compound selected from the group consisting of 91
-continued
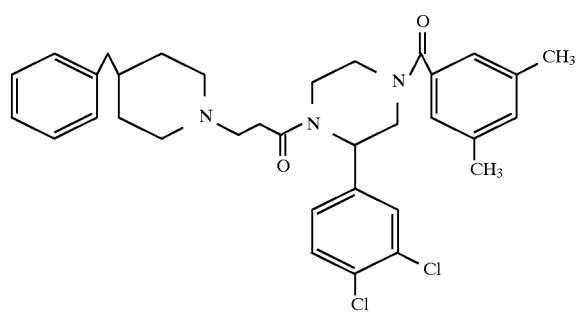
92
-continued
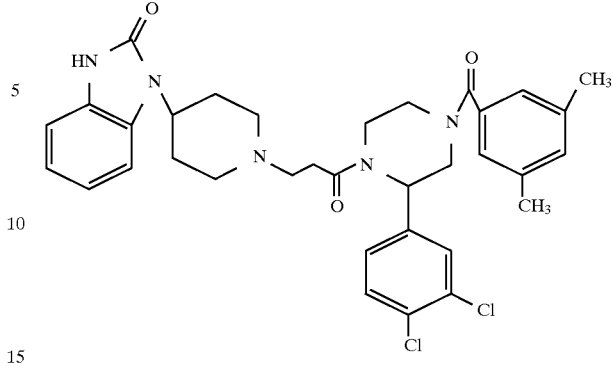
or a pharmaceutically acceptable salt thereof.
* * * * *